United States Patent
Lyng et al.

(10) Patent No.: US 10,725,017 B2
(45) Date of Patent: Jul. 28, 2020

(54) PREDICTION OF THERAPEUTIC RESPONSE USING VIBRATIONAL SPECTROSCOPY

(71) Applicant: Technological University Dublin, Dublin (IE)

(72) Inventors: Fiona Lyng, Dublin (IE); Adrian Maguire, Kildare (IE); Aidan Meade, Dublin (IE); Isabel Vega Carrascal, Dublin (IE); Lisa White, Down (GB); Orla Howe, Dublin (IE)

(73) Assignee: Technological University Dublin, Dublin (IE)

( * ) Notice: Subject to any disclaimer, the term of this patent is extended or adjusted under 35 U.S.C. 154(b) by 0 days.

(21) Appl. No.: 16/064,412

(22) PCT Filed: Dec. 20, 2016

(86) PCT No.: PCT/EP2016/081900
§ 371 (c)(1),
(2) Date: Jun. 20, 2018

(87) PCT Pub. No.: WO2017/108775
PCT Pub. Date: Jun. 29, 2017

(65) Prior Publication Data
US 2018/0372710 A1    Dec. 27, 2018

(30) Foreign Application Priority Data

Dec. 21, 2015 (GB) .................... 1522557.6

(51) Int. Cl.
*G01N 33/483* (2006.01)
*G01N 33/49* (2006.01)
(Continued)

(52) U.S. Cl.
CPC ......... *G01N 33/4833* (2013.01); *A61N 5/103* (2013.01); *G01N 21/3563* (2013.01);
(Continued)

(58) Field of Classification Search
CPC .......... G01N 33/4833; G01N 21/3563; G01N 21/3577; G01N 21/65; G01N 33/49; G01N 33/54366; G01N 33/574; A61N 5/103
(Continued)

(56) References Cited

U.S. PATENT DOCUMENTS

| 2009/0042229 A1 | 2/2009 | Folkman et al. |
| 2014/0012514 A1 | 1/2014 | Roder et al. |
| 2019/0218308 A1* | 7/2019 | Chanteux ............... C07K 16/40 |

FOREIGN PATENT DOCUMENTS

| WO | WO-2008149119 A1 | 12/2008 |
| WO | WO-2010096680 A2 | 8/2010 |

(Continued)

OTHER PUBLICATIONS

Denham, J.W., et al., "Recognizing False Biochemical Failure Calls after Radiation with or without Neo-Adjuvant Androgen Deprivation for Prostate Cancer," Int. J. Radiation Oncology Biol. Phys., vol. 74, No. 2, 2009, pp. 404-411.
(Continued)

*Primary Examiner* — Roy M Punnoose
(74) *Attorney, Agent, or Firm* — Ross T. Robinson

(57) ABSTRACT

The invention relates to a prognostic method of analyzing a biological sample from a cancer patient to predict his/her response to a specified modality of cancer treatment comprising the steps of: (a) performing spectroscopy on the biological sample to obtain a spectrum; (b) comparing the obtained spectrum with one or more spectra to calculate a probability of a response to the specified modality of cancer treatment by the cancer patient.

20 Claims, 15 Drawing Sheets

(51) Int. Cl.
| | |
|---|---|
| *G01N 21/65* | (2006.01) |
| *G01N 33/543* | (2006.01) |
| *G01N 33/574* | (2006.01) |
| *G01N 21/3563* | (2014.01) |
| *A61N 5/10* | (2006.01) |
| *G01N 21/3577* | (2014.01) |
| *G01N 21/35* | (2014.01) |

(52) U.S. Cl.
CPC ......... *G01N 21/3577* (2013.01); *G01N 21/65* (2013.01); *G01N 33/49* (2013.01); *G01N 33/54366* (2013.01); *G01N 33/574* (2013.01); *G01N 2021/3595* (2013.01); *G01N 2201/129* (2013.01); *G01N 2800/52* (2013.01)

(58) Field of Classification Search
USPC .......................................................... 356/39
See application file for complete search history.

(56) References Cited

FOREIGN PATENT DOCUMENTS

| WO | WO-2011121588 A1 | 10/2011 |
|---|---|---|
| WO | WO-2011151825 A2 | 12/2011 |
| WO | WO-2013001507 A2 | 1/2013 |
| WO | WO-2014076480 A1 | 5/2014 |
| WO | WO-2014154854 A1 | 10/2014 |

OTHER PUBLICATIONS

Lakshmi, R. J., et al., "Tissue Raman Spectroscopy for the Study of Radiation Damage: Brain Irradiation of Mice," Radiation Research, vol. 157, 2002, pp. 175-182.

Matthews, Q., et al., "Raman Spectroscopy of Single Human Tumour Cells Exposed to Ionizing Radiation In Vitro," Physics in Medicine and Biology, vol. 56, 2011, pp. 19-38.

Schnarr, K., et al., "Radiation-Induced Lymphocyte Apoptosis to Predict Radiation Therapy Late Toxicity in Prostate Cancer Patients," Int. J. Radiation Oncology Biol. Phys., vol. 74, No. 5, 2009, pp. 1424-1430.

Hoesel, Heidi, "International Search Report," prepared for PCT/EP2016/081900, dated Jun. 2, 2017, eight pages.

Wald, N., et al., "Infrared Spectra of Primary Melanomas Can Predict Response to Chemotherapy: The Example of Dacarbazine," Biochimica et Biophysica Acta. Molecular Basis of Disease, vol. 1862, No. 2, Nov. 11, 2015, pp. 174-181.

Matthews, Q., et al., "Radiation-Induced Glycogen Accumulation Detected by Single Cell Raman Spectroscopy Is Associated with Radioresistance that Can Be Revsed by Metformin," PLOS ONE, vol. 10, No. 8, Aug. 17, 2015, pp. 1-15.

Matthews, Q., et al., "Biochemical Signatures of In Vitro Radiation Response in Human Lung, Breast and Prostate Tumour Cells Observd with Raman Spectroscopy," Physics in Medicine and Biology, Institute of Physic Publishing, Bristol GB, vol. 56, No. 21, Oct. 5, 2011, pp. 6839-6855.

Ramos, I.R.M., et al., "Current Advances in the Application of Raman Spectroscopy for Molecular Diagnosis of Cervical Cancer," BioMed Research International, 2015, pp. 1-9.

Zendehdel R., et al., "Patterns Prediction of Chemotherapy Sensitivity in Cancer Cell Lines Using FTIR Spectrum, Neural Network and Principal Components Analysis," Iranian Journal of Pharmaceutical Research, vol. 11, No. 2, 2012, pp. 401-410.

Harder, S. J., et al., "Raman Spectroscopy Identifies Radiation Response in Human Non-Small Cell Lung Cancer Xenografts," Scientific Reports, vol. 6, Feb. 17, 2016, pp. 1-10.

Kaur, E., et al., "Unique Spectral Markers Discern Recurrent Glioblastoma Cells From Heterogeneous Parent Population," Scientific Reports, vol. 6, May 25, 2016, 14 pages.

* cited by examiner

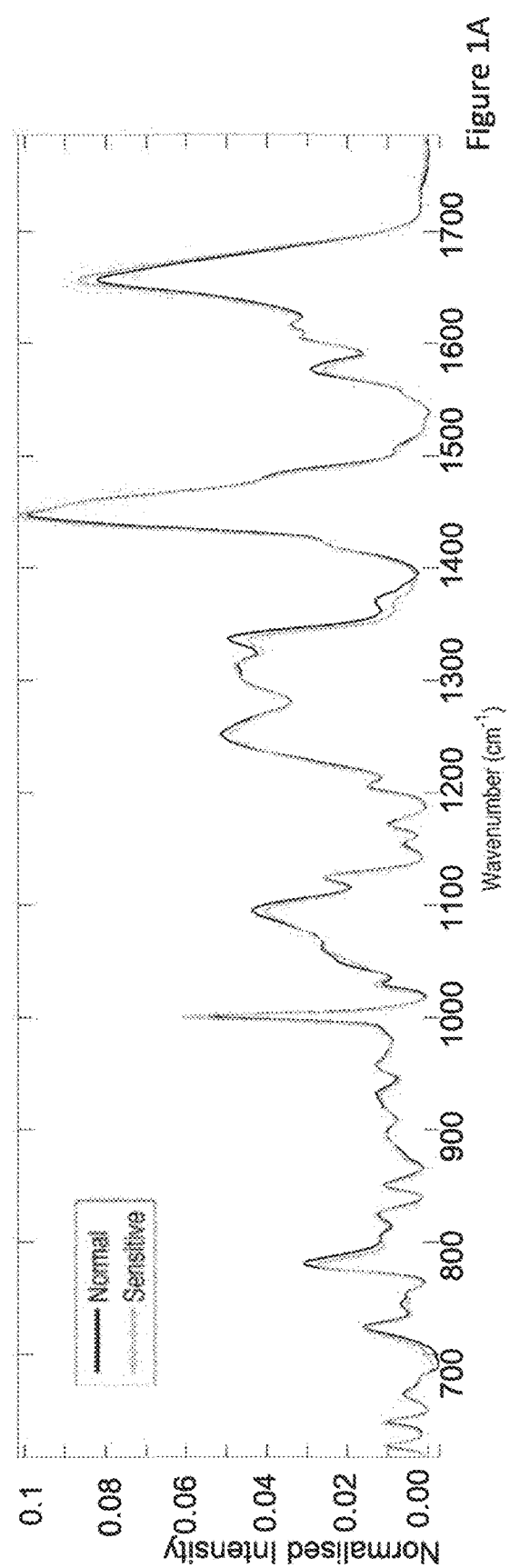
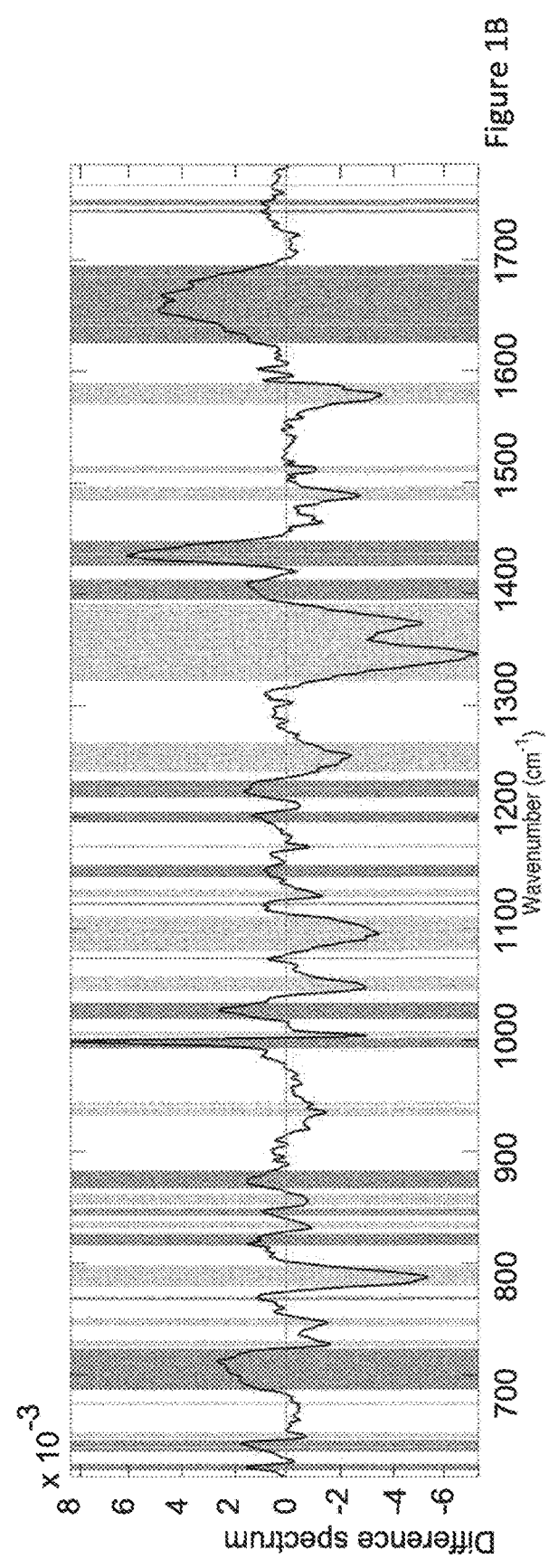

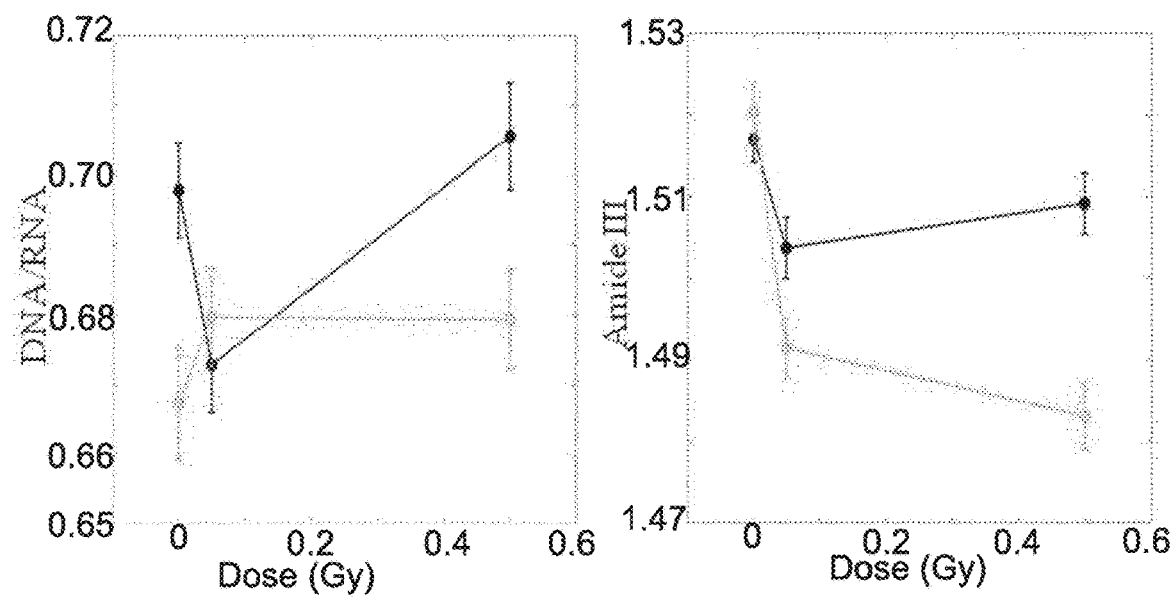
Band Area of 770 - 795 cm$^{-1}$
Figure 2A
Band Area of 1239 - 1273 cm$^{-1}$
Figure 2B
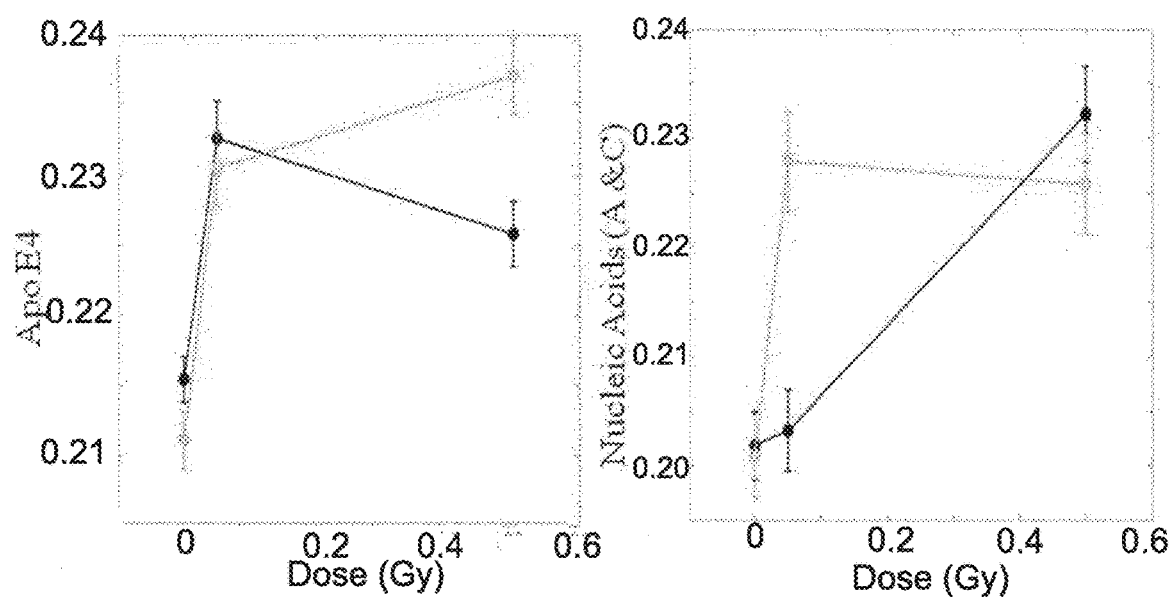
Band Area of 970 - 980 cm$^{-1}$
Figure 2C
Band Area of 1504 - 1535 cm$^{-1}$
Figure 2D Band Area of 1079 − 1110 cm$^{-1}$      Band Area of 1630 − 1690 cm$^{-1}$

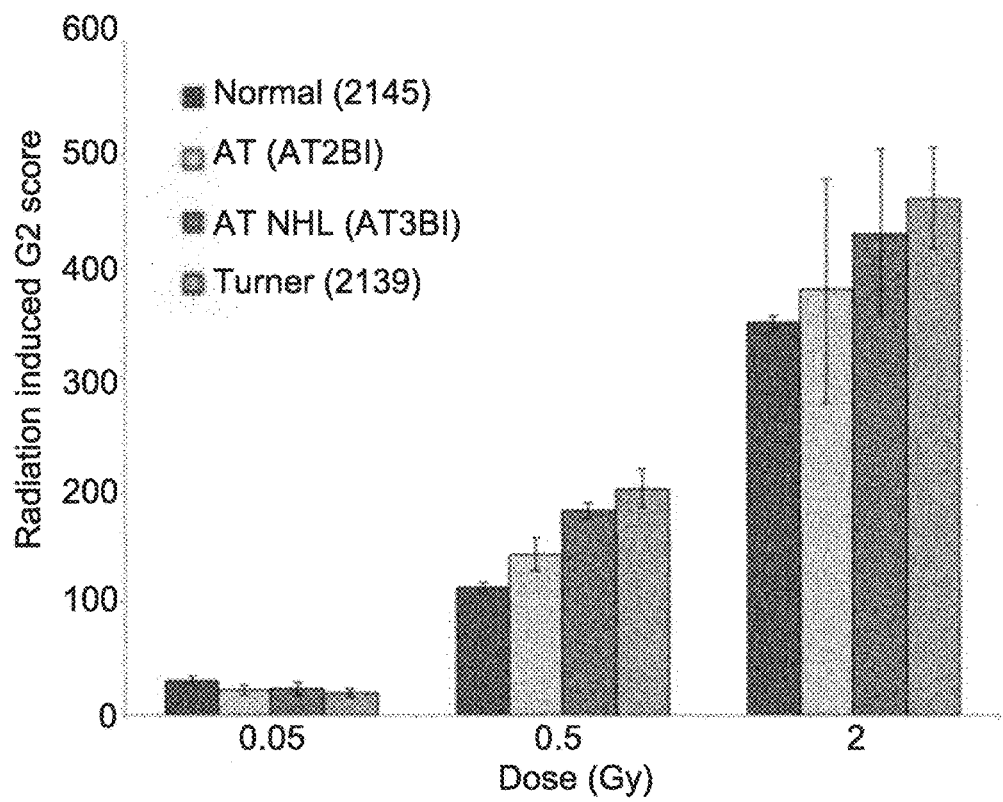
Figure 5
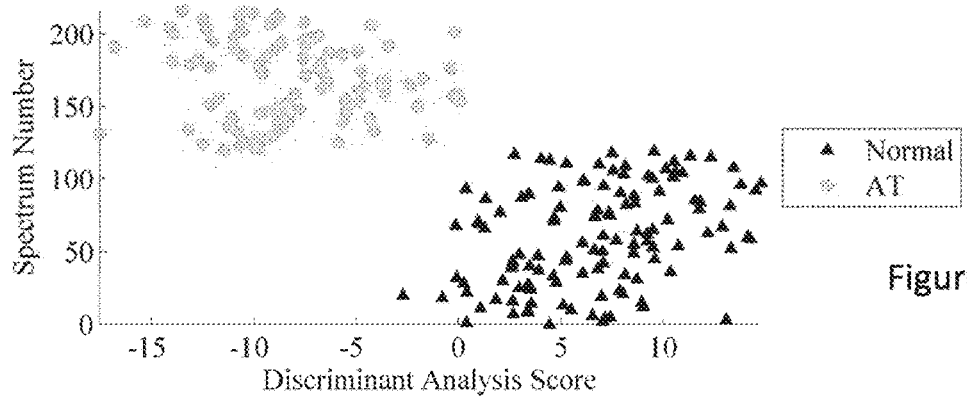
Figure 6A(i)
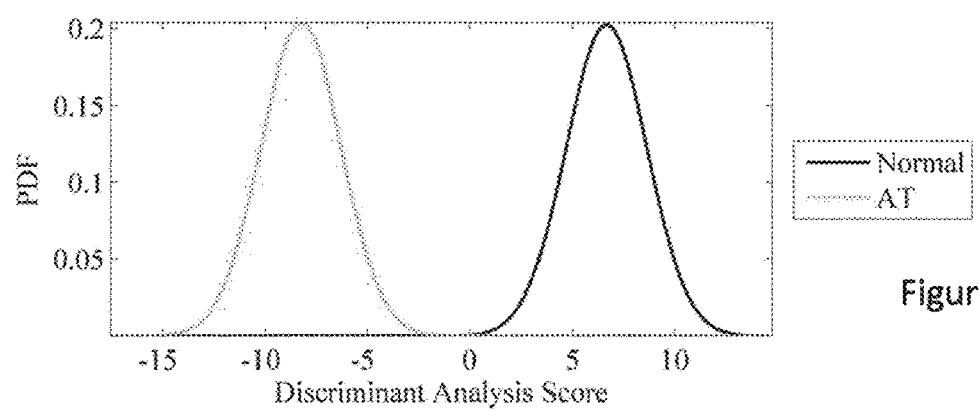
Figure 6A(ii)

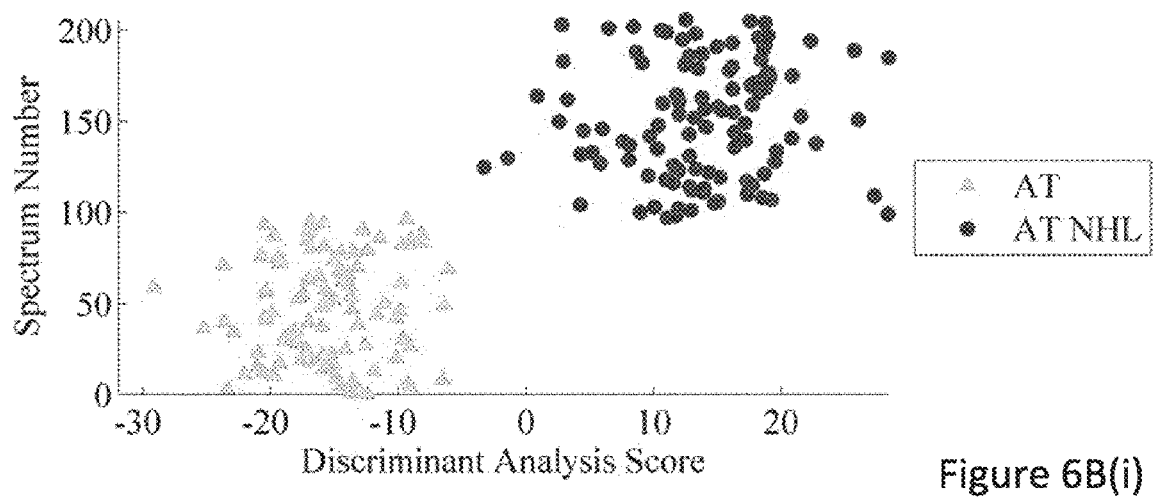
Figure 6B(i)
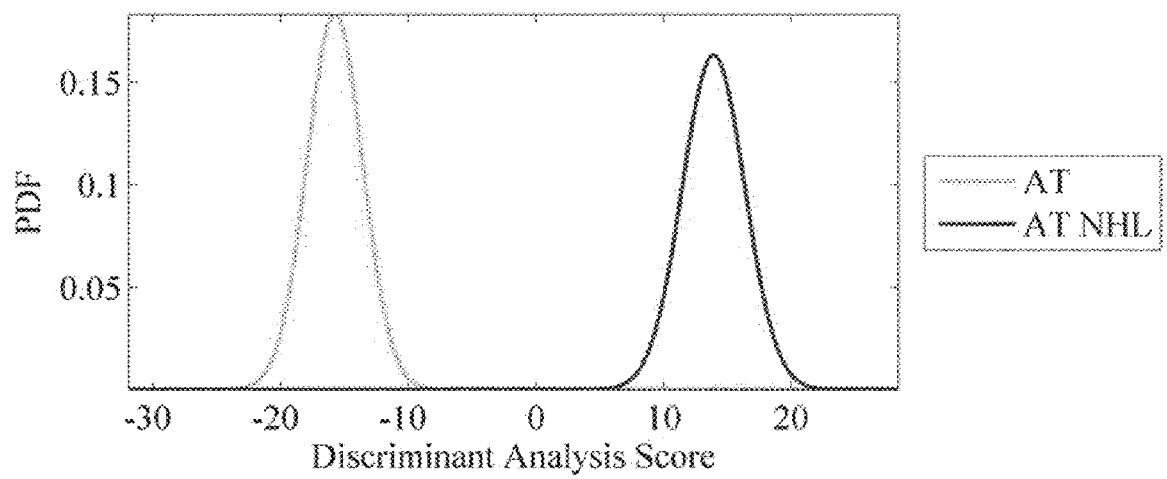
Figure 6B(ii)

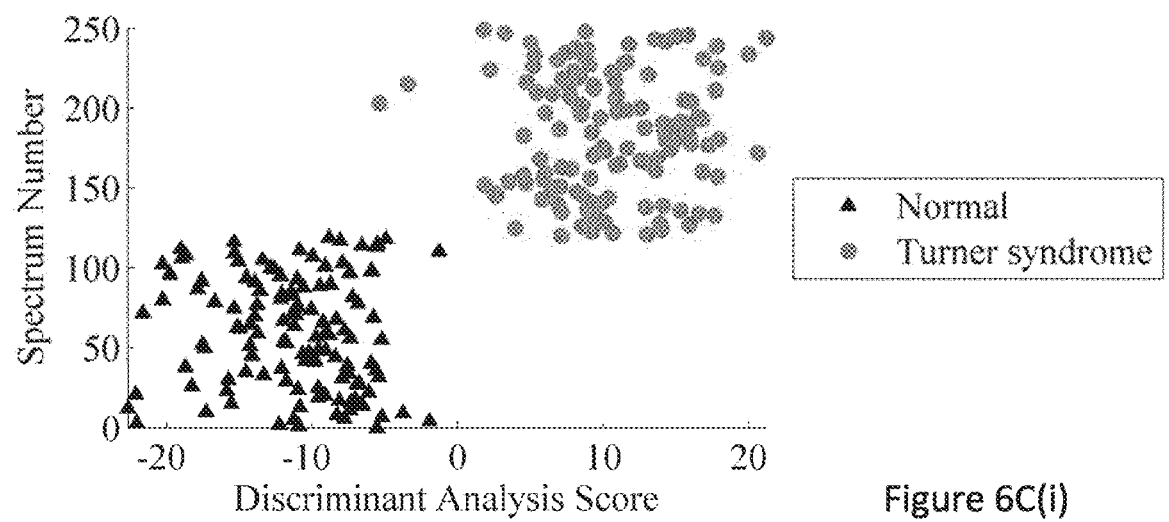
Figure 6C(i)
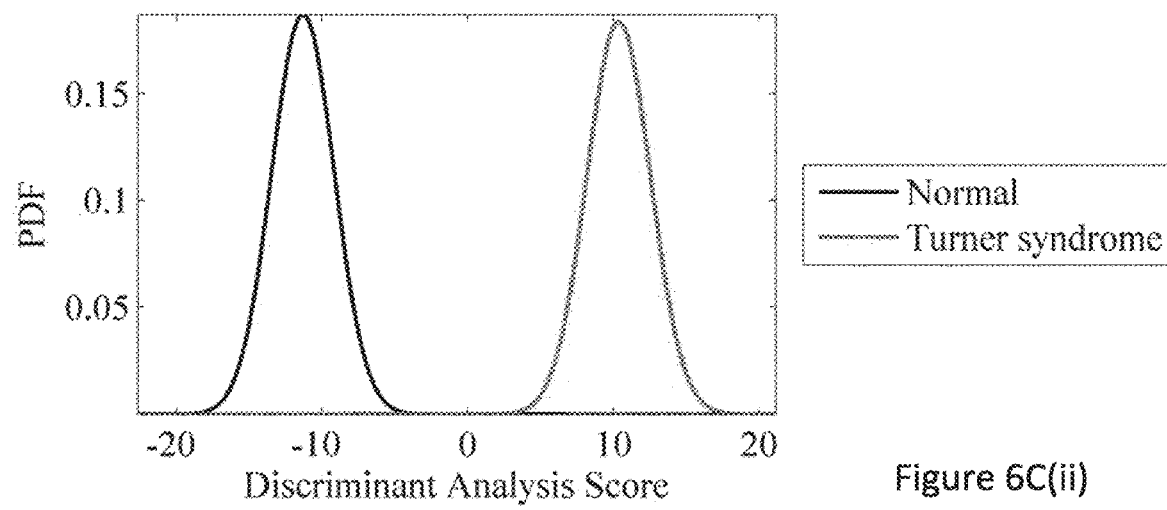
Figure 6C(ii)

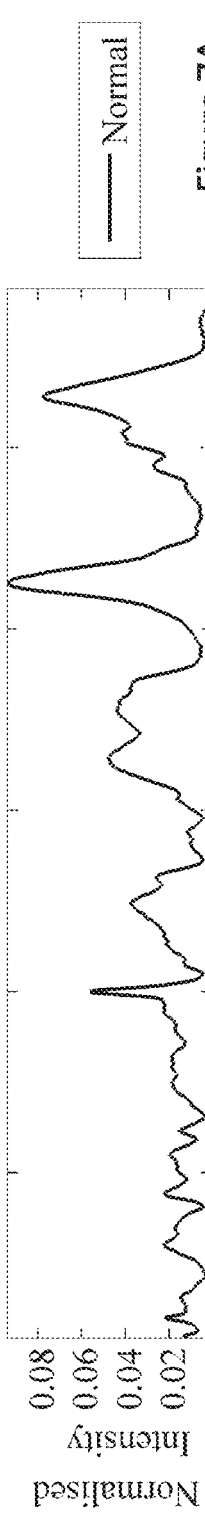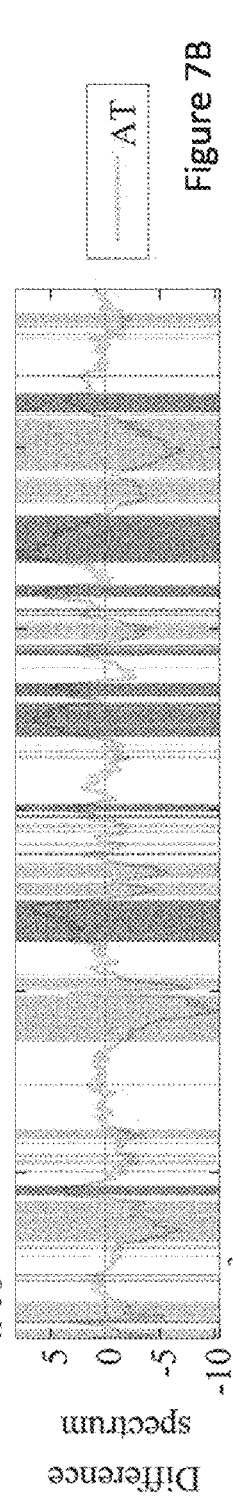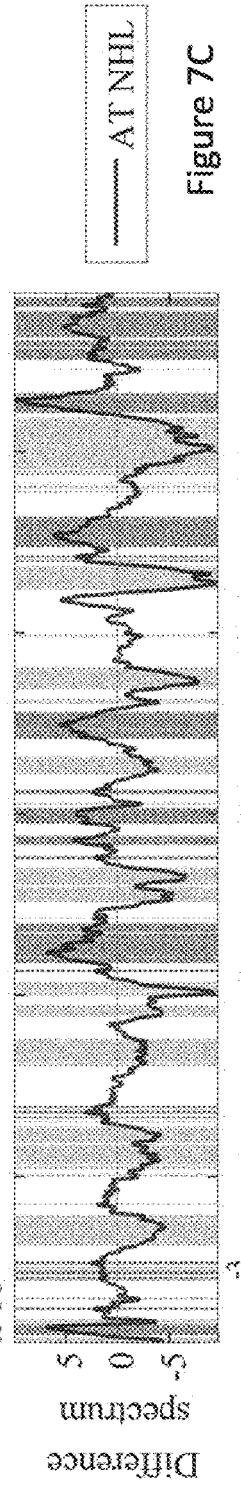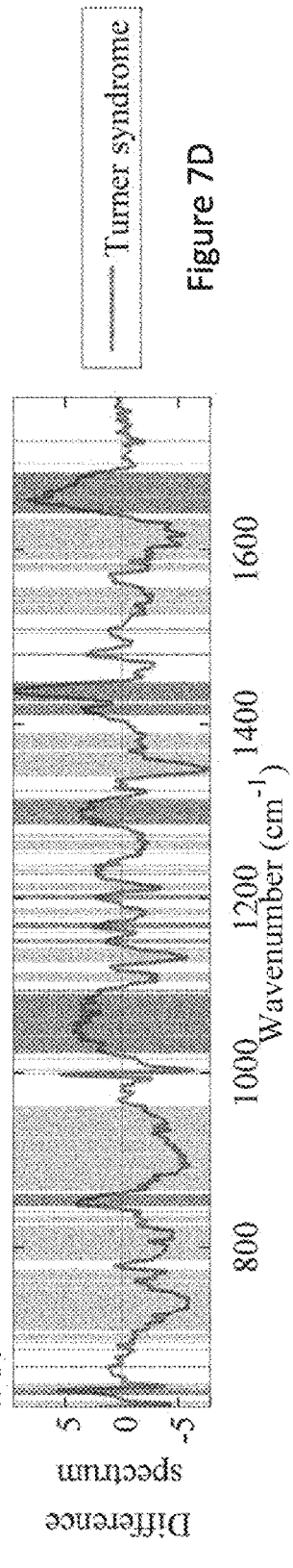

PREDICTION OF THERAPEUTIC RESPONSE USING VIBRATIONAL SPECTROSCOPY

FIELD OF THE INVENTION

The present application is directed to identifying the likelihood of full pathological treatment response, cancer recurrence or treatment toxicity in patients undergoing radiation therapy using vibrational spectroscopy.

BACKGROUND

According to Globocan 14.1 million new cancer cases occur worldwide of which 3.2 million cases are seen in Europe[1]. In radiotherapy, response is governed largely by the intrinsic radiosensitivity of the patient, which varies by cancer type. Despite the treatment being standard for around half[2] of all cancer patients, the full-response rate to the treatment can be as low as 20% in gastrointestinal cancer[3], and 15% in breast cancer[4]. Adverse side effects from treatment could be reduced if alternatives to radiotherapy could be considered in patients where little to no response is expected.

Each cancer patient has a unique response to treatment. An individual patient's response to cancer treatment is, to a significant degree, determined by their own biology (genetic profile) and other environmental factors such as diet and lifestyle. With the evolution of technologies such as gene sequencing and associated computational methods, it is now possible to link a patient's biological profile and lifestyle characteristics to measurements of their treatment response. This can supply clinicians with a prediction of the risk of recurrence or probability of regression of cancer for a particular patient and for a particular treatment option. The prescription of an individualised therapeutic plan to cancer patients strongly depends on the identification of clinical and biological characteristics that can be used to stratify patients in terms of their probability of therapeutic success[5]. Researchers have, for the past two decades, attempted to identify clinical and molecular biomarkers for a range of cancer types which can reveal key factors that influence the progression of disease and its resistance to chemotherapeutic or radiotherapeutic treatment[6]. An additional and parallel aim has been to use biomarkers identified in such studies as potential chemo-therapeutic targets[7].

There have been many approaches that have been adopted to satisfy this objective. One has been to analyse expression profiles at a genomic and proteomic level with a view to classification of individual patients into clinical subtypes based on probable response[8-10]. An alternative approach has been to utilize immunohistochemical imaging approaches with image segregation algorithms to produce standardized measurements of antibody staining profiles[11,12] as metrics of patient treatment success. This latter approach has been relatively successful with prognostic performance similar to that of more complex approaches[13,14]. However, in its totality, these efforts have had limited success in this regard owing to challenges surrounding study design and power[15-17], with the result that prognostic markers for many cancer types have not seen widespread adoption and successful use in clinics.

The present invention seeks to alleviate the disadvantages of the prior art in this field. It does so by developing procedures and processes within a test, which allows the objective of prediction of treatment response in cancer patients.

The present method allows the analysis of a variety of sample types including crude biological samples (i.e., not purified or processed or refined and in a natural state). The method can work with samples of blood or blood constituents. The samples may be tissue sections, where whole cells are arranged substantially as they were in their original state. The samples may contain whole cells or cells that have been lysed, either chemically or mechanically. The samples may include cells that are still alive at the time of analysis. The samples may also be fixed or preserved or processed. In some embodiments the samples may be irradiated prior to analysis. The term "prognostic" is used in this specification to mean relating to the prediction of the likely course of a medical condition. This includes the course of the medical condition when treated, including whether the condition improves in response to the treatment and if there are side effects in response to the treatment.

In the description of the invention we refer to "spectral biomarkers", which requires definition here. A "spectral biomarker" is not the same as a "molecular biomarker". A spectral biomarker is a region in a spectrum or a pattern in a spectrum obtained from a sample which is correlated with a characteristic of interest. A spectral biomarker is not necessarily indicative of the presence or absence or concentration of any one particular biomolecule. Spectral biomarkers are not typically assigned to any specific biomolecule, in part due to the fact that the biomolecules which impart the characteristics of interest are not observable in crude (i.e., not purified) sample analysis such as vibrational spectroscopy due to the overlapping vibrational spectra of thousands of chemicals; and also because the biomolecules which impart the characteristics of interest may not be explicitly known. These unassigned and often unknown underlying features of the biochemistry of a sample may nonetheless leave a spectral biomarker correlating to a characteristic of interest which is discernible through statistical analysis of the spectra, or "frequent pattern mining"14. These spectral biomarkers may then be used in a triage process.

The present invention relates to the features disclosed in the following numbered statements:

1. A prognostic method of analyzing a biological sample from a cancer patient to predict his/her response to a specified modality of cancer treatment comprising the steps of:
    (a) performing spectroscopy on the biological sample to obtain a spectrum;
    (b) comparing the obtained spectrum with one or more pre-classified spectra to calculate the probability of a response to the specified modality of cancer treatment by the cancer patient.
2. The method of statement 1 wherein the modality of cancer treatment comprises radiotherapy.
3. The method of statement 1 wherein the modality of cancer treatment comprises radiotherapy combined with either chemotherapy or hormonal therapy.
4. The method of statement 1 wherein the modality of cancer treatment comprises chemotherapy.
5. The method of statement 1 wherein the modality of cancer treatment comprises hormonal therapy.
6. A method according to any one of the preceding statements, wherein the sample is a crude biological sample. In some embodiments the sample does not require chemical processing or fixing. This has the advantage of fewer steps than methods which require processing and thus faster turnover.
7. A method according to any one of the preceding statements, wherein the sample comprises whole cells. These cells may be tumour cells from a tumour biopsy or lymphocytes from a blood sample or exfoliated oral cells for example. The whole cells may also comprise other tissue cells as the spectral biomarkers of radiosensitivity are not necessarily specific to tumour cells.

8. A method according to any one of the preceding statements, wherein the sample comprises live cells. The cells may still be alive during analysis after minimal or no processing as FTIR and Raman spectroscopy are not lethal.

9. A method according to any of the preceding statements wherein the biological sample is not irradiated prior to the spectroscopy analysis. This has the advantage of safety for the person carrying out the test, the method taking less time and thus higher turnover.

10. A method according to any one of the preceding statements, wherein the sample is a tissue sample. This may be a biopsy from a tumour for example.

11. A method according to statement 1, wherein the tissue sample is a formalin fixed-paraffin preserved tissue sample. Fixation preserves the sample and allows the analysis to be done some time after obtaining the sample from the patient. Formalin fixation does not interfere with the spectroscopy or the imaging. The same sample may be used for traditional histology and for Raman or FTIR imaging and regular Raman or FTIR spectroscopy.

12. A method according to statement 11 in which the tissue sample is a microtomed tissue section mounted on a spectroscopic substrate. This ensures the uniformity of samples and the quality of the spectroscopy.

13. A method according to statement 12 in which the tissue sample is a 10 μm thick tissue section mounted on a spectroscopic substrate.

14. A method according to any one of statements 1 to 9, wherein the sample comprises a biofluid including blood; blood constituents; and also other biofluids including, but not limited to urine, saliva. Such biofluid samples have the advantage of being easily obtained from a patient. Furthermore, the sample for use in the prognostic method of the present invention may comprise a whole blood sample. This is significantly advantageous for ease of use of the prognostic method of the present invention.

15. A method according to any one of statements 1 to 9, wherein the sample is contained within a microwell plate. The sample may be used in other forms of biological testing and analysis subsequently.

16. A method according to any one of statements 1 to 9, wherein the sample is a blood lymphocyte sample. This has the advantage over whole blood of not having red blood cells, which have vibrational spectra which may mask or overlap with certain spectral biomarkers in certain embodiments.

17. A method according to any one of the preceding statements wherein the spectroscopy is vibrational spectroscopy. This has the advantages of being cost-effective, fast, suitable for mixtures, quantitative, suitable for imaging and that it does not damage the sample or require extensive processing of the sample. The sample may subsequently be used for other forms of analysis.

18. A method according to statement 17 wherein the vibrational spectroscopy is performed using Raman spectroscopy. This has the advantages of being cost-effective, fast, suitable for mixtures, quantitative, suitable for imaging and also that it does not damage the sample or require extensive processing of the sample. The sample may subsequently be used for other forms of analysis.

19. A method according to statement 17 wherein the vibrational spectroscopy is performed using FTIR spectroscopy. This has the advantages of being cost-effective, fast, suitable for mixtures, quantitative, suitable for imaging and that it does not damage the sample or require extensive processing of the sample. The sample may subsequently be used for other forms of analysis.

20. A method according to statement 17 wherein the vibrational spectroscopy is performed using FTIR imaging. The imaging may be used as an adjunct to the spectral analysis. For example, in one embodiment the FTIR imaging is used to select a point or group of points on the image form which a useful FTIR spectrum for analysis may be obtained. The imaging may additionally be used as part of a histological analysis of a tumour.

21. A method according to statement 17 wherein the vibrational spectroscopy is performed using Raman imaging. The imaging may be used as an adjunct to the spectral analysis. For example, in one embodiment the Raman imaging is used to select a point or group of points on the image form which a useful Raman spectrum for analysis may be obtained. The imaging may additionally be used as part of a histological analysis of a tumour.

22. The method of statement 1 wherein the response to cancer treatment comprises tumour regression.

23. The method of statement 22 wherein the response to cancer treatment comprises complete tumour regression.

24. The method of statement 22 wherein the response to cancer treatment comprises partial tumour regression.

25. The method of statement 22 wherein the response to cancer treatment comprises intermediate tumour regression.

26. The method of any preceding statement wherein the response to cancer treatment comprises unwanted side effects.

27. The method of statement 26 wherein the response to cancer treatment comprises radiotherapeutic treatment toxicity.

28. The method of statement 26 wherein the response to cancer treatment comprises chemotherapeutic treatment toxicity.

29. A method according to statement 1, wherein the step of comparing comprises the use of spectral decomposition followed by analysis by a classifier.

30. A method according to statement 29, wherein the spectral decomposition comprises the use of principal component analysis (PCA) spectral decomposition.

31. A method according to statement 29, wherein the classifier is a Linear Discriminant analysis classifier.

32. A method according to statement 31, wherein the Linear Discriminant analysis classifier is a Fisher's Linear Discriminant classifier.

33. A method according to statement 29, wherein the classifier is a Quadratic Discriminant analysis classifier.

34. A method according to statement 33, wherein the Quadratic Discriminant analysis classifier is a Fisher's Quadratic Discriminant classifier.

35. A method according to statement 29, wherein the classifier is a support vector machine classifier.

36. A method according to statement 29, wherein the classifier is a decision tree classifier.

37. A method according to statement 29, wherein the classifier is a neural network.

38. A method according to statement 14, further comprising the step of culturing the blood lymphocyte cells as whole blood in-vitro.

39. A method according to statement 14, further comprising the step of irradiating the in-vitro blood sample. This allows the detection of certain changes that occur upon irradiation of the sample. An irradiated sample may be compared to a non-irradiated sample in some embodiments.
40. A method according to statement 32, further comprising extracting lymphocytes from the irradiated sample.
41. A method according to statement 34, further comprising the step of fixing the lymphocytes and wherein the step of performing spectroscopy is carried out on the fixed lymphocyte material.
42. A method according to any preceding statement, wherein the cancer is oesophageal cancer.
43. A method according to any preceding statement, wherein the cancer is colorectal cancer.
44. A method according to any one of statements 1 to 42, wherein the cancer is prostate cancer.
45. A method according to any one of statements 1 to 35, wherein the cancer is breast cancer.
46. A method according to any of the preceding statements wherein the cancer patient is a mammal.
47. A method according to any of the preceding statements wherein the cancer patient is a human.
48. A method according to statement 26 wherein the response to cancer treatment comprises normal tissue toxicity.
49. A method according to statement 26 wherein the adverse effects are classified according to standard toxicity scoring systems such as CTCAE or RTOG or similar.

In cases where the cancer comprises a solid tumour and a biopsy of the tumour has been taken, the following biopsy and imaging method steps are carried out:
A. obtaining diagnosis of a cancer patient;
B. obtaining sample via tumour biopsy;
C. subjecting sample to fixation and paraffin embedding;
D. performing microtoming on sample;
E. acquiring FTIR/Raman spectra;
F. analysing obtained images by a statistical learning algorithm which compares obtained spectra to spectra from a pre-classified library; and
G. predicting response to therapy.

The step of acquiring FTIR or Raman imaging of the sample may comprise obtaining spectra from many points in the sample. The Acquisition step (imaging) may comprise histological analysis and selection of a point or group of points on the sample from which the vibrational spectra will be analysed in later steps.

In cases where a blood sample is taken from a patient, the blood sample may be used whole and analysed or the plasma may be extracted and analysed or the lymphocytes may be extracted and analysed.

The steps for analysing plasma are as follows:
i. obtaining diagnosis of a cancer patient;
ii. obtaining blood sample;
iii. extracting serum or plasma;
iv. depositing serum or plasma on substrate;
v. acquiring Raman/FTIR spectra;
vi. analysing obtained spectra by a statistical learning algorithm which compares obtained spectra to spectra from a pre-classified library; and
vii. predicting response to therapy.

The steps for analysing lymphocytes are as follows:
a. obtaining diagnosis of a cancer patient;
b. obtaining blood sample;
c. extracting lymphocytes;
d. fixing lymphocytes;
e. depositing fixed lymphocytes on substrate;
f. acquiring Raman/FTIR spectra;
g. analysing obtained spectra by a statistical learning algorithm which compares obtained spectra to spectra from a pre-classified library; and
h. predicting response to therapy.

Optionally, the above method of analysing lymphocytes may comprise the additional step of isolating peripheral blood mononuclear cells (PBMC), carried out after step (b). Other blood components may be present during analysis.

The method may also comprise the step of subjecting whole blood sample to in-vitro gamma-irradiation; in which the lymphocytes are given a challenge dose of gamma radiation is optional. The lymphocytes may be analysed without in-vitro gamma-irradiation.

In accordance with statement 1 above, the present application has the advantage of providing a test having high specificity and sensitivity that estimates the probability of response to treatment for a wide range of cancers. Thus, two alternative approaches may be used in accordance with the method of the present invention as will become further apparent from the following disclosure.

SUMMARY

The present application provides a method having the following features:
- This technology provides the means to predict the likelihood of a patient with a tumour to develop a favourable response to therapy. This method involves the measurement of the vibrational spectra (Raman or infrared) of the tumour tissue extracted through biopsy of the patient or the measurement of the vibrational spectra (Raman or infrared) of peripheral blood drawn from the patient;
- As will be described, in another aspect of the present invention, the present invention provides means for predicting the likelihood that the patient possesses high levels of intrinsic radiosensitivity which are linked to increased likelihood of adverse response in cancer patients.
- As will be described, in a further aspect, the present invention also provides means for predicting the likelihood that the patient will develop acute or late toxicity from the therapy.
- The therapy may comprise radiotherapy or combination therapies including hormone radiotherapy and chemo-radiotherapy.
- The tumour may be any tumour or cancer such as an oesophageal tumour, a colorectal tumour or a prostate tumour.
- In addition, the present invention provides means for monitoring the progress of treatment within the course of therapy using vibrational spectra of peripheral blood extracted from the patient.

BRIEF DESCRIPTION OF THE DRAWINGS

FIG. 1 shows the mean Raman spectra of lymphocytes in normo-sensitive and radiosensitive individuals (FIG. 1A) and difference spectrum of normal and radiosensitive individuals (FIG. 1b); the shaded regions represent where the difference spectrum was found to be significantly different using a 2-tailed Students t-test with p<0.005.

FIGS. 2A to 2F inclusive illustrate the band areas differentiating lymphocytes in normo-sensitive and radiosensitive individuals;

FIG. 2A specifically details the band area of 770-795 cm$^{-1}$ which is assigned to DNA and RNA;

FIG. 2B specifically details the band area of 1239-1273 cm$^{-1}$ which is assigned to Amide III;

FIG. 2C specifically details the band area of 970-980 cm$^{-1}$ which is assigned to ApoE4;

FIG. 2D specifically details the band area of 1504-1535 cm$^{-1}$ which is assigned to nucleic acids A and C;

FIG. 2E specifically details the band area of 1079-1110 cm$^{-1}$ which is assigned to the O—P—O functional group of the phosphate backbone of DNA;

FIG. 2F specifically details the band area of 1630-1690 cm$^{-1}$ which is assigned to Amide I;

FIG. 4 is the depiction of a consensus classifier for the discrimination of prostate cancer patients on the basis of their radiotherapeutic treatment toxicity using Raman spectra of their lymphocytes and plasma.

FIG. 5 is a bar chart of the radiosensitivity of normal cells, AT2BI cells, AT3BI cells and Turner cells at varying doses of radiation measured by a radiation induced G2 chromosomal abberation assay;

FIGS. 6A to 6C are the linear discriminant analysis results of various cells types LOOCV classification; FIG. 6Ai displays normal versus Ataxia Telangiectasia (AT); 5Bi illustrates AT versus AT Non-Hodgkins Lymphoma (NHL); FIG. 6Ci illustrates normal versus Turner syndrome; Bottom panels (6Aii, 6Bii, 6Cii) show the respective probability distribution functions for each cell type;

FIG. 7A is a Raman spectrum of a normal cell line;

FIGS. 7B to 7D are difference spectra of normal cells and non-normal cells. Shaded regions represent where the spectra of normal cells were significantly higher (dark) or lower (light) than all other cell types. Significance level is p<0.005:

FIG. 7B is the difference spectrum of a normal cell line and AT cell line;

FIG. 7C is the difference spectrum of a normal cell line and AT NHL cell line;

FIG. 7D is the difference spectrum of a normal cell line and Turner Syndrome cell line; Finally, FIGS. 8A-8C demonstrate the capability of the Raman spectroscopic technique to discriminate patients on the basis of their response to adjuvant chemo-radiotherapy (tissue regression grade, TRG status) using Raman spectra of their stromal tissue acquired at biopsy. Shading shows areas where statistically significant differences between the spectra were seen using a t-test with a significance level of p<0.005:

DETAILED DESCRIPTION

Figure 2E:
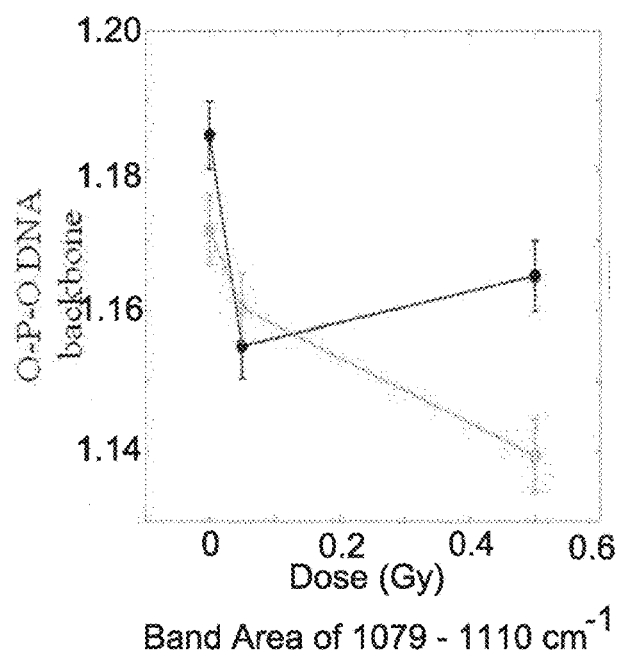
Figure 2F:
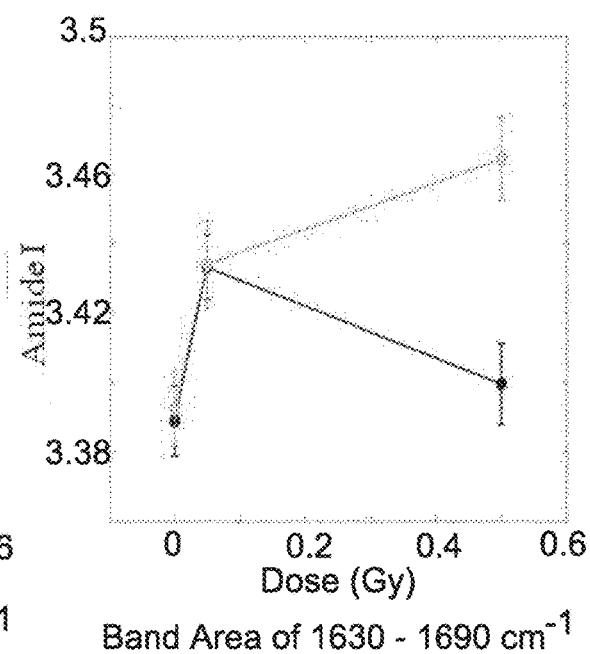

The present application provides a solution to the previously identified problems associated with the current state of the art. In preferred embodiments, the present invention provides a method of testing that indicates whether a cancer patient is likely to respond with a complete pathological response to chemo-radiotherapy; as well as likely to respond adversely to radiation therapy and in addition whether the patient has high levels of intrinsic radiosensitivity.

For example, neo adjuvant chemo-radiotherapy is employed for oesophageal and rectal cancer to de-bulk tumour size in advance of conducting surgery. However, a treatment response only occurs in approximately 20% of patients, with little or no response in the remaining 80% of patients. Because of this, many patients receive the treatment with little or no benefit to them. However, they have an elevated risk of radiation induced toxicity. The present application is directed at providing a predictive methodology that separates patient populations into responders and non-responders, i.e. based on whether the patient is likely to respond positively to the treatment.

The prognostic method of the present invention employs spectroscopy, suitably Raman or FTIR spectroscopic imaging, for the prediction of the response of patients to therapy.

In one embodiment of the present invention, the method of prediction of the response of patients to therapy may be carried out, using samples of the patient's tumour tissue where the tissue is preserved by snap-freezing or formalin-fixation paraffin-embedding etc. The tissue block is then sectioned using a microtome into a 4-12 micron thickness onto spectroscopic substrates (for example, calcium fluoride, CaF$_2$) or glass slides. Spectroscopic images of tissue are acquired either by histological guide, or spectra from specific regions of interest are extracted by image segmentation. The spectra are pre-processed (calibration, baseline removal, standardisation). Subsequently, the spectra are delivered to a classification algorithm which returns a probability that the patient will develop an adverse reaction to the radiotherapeutic treatment, and a probability that the patient will develop a full pathological response to the treatment, and a probability that the patient has high levels of radiosensitivity. The classification may be performed using supervised learning (support vector machines, naïve Bayes classifiers, neural networks, random forests, Fisher's linear discriminant analysis). In a preferred embodiment, this classification is performed using Principal Components Analysis Linear Discriminant Analysis.

In another embodiment of the method of the present invention, the method of prediction of the response of patients to therapy may be carried out by taking a sample of peripheral blood from the patient. In one of these embodiments, a spectrum is taken of the extracted lymphocyte fraction which is then input to a supervised learning algorithm. This algorithm has its basis in statistical learning theory, where the algorithm classifies spectra into various classes on the basis of relationships between spectra and classes that it has previously established in the learning or supervised training phase. In another of these embodiments, the whole blood sample is cultured in-vitro for 3 days. The blood is then irradiated in-vitro, along with a sham-irradiated control (i.e. a sample subjected to all of the conditions that an irradiated sample is subjected to such as changes in temperature and being transferred to a different container, but without being irradiated), and returned to culture. One hour after irradiation, the lymphocyte fraction is separated from the whole blood and chemically fixed in paraformaldehyde to preserve the cells. The lymphocytes are then deposited onto spectroscopic substrates (calcium fluoride, $CaF_2$) or glass slides. Whole cell spectra of a randomly selected sample of the lymphocytes are taken. These spectra are measured using a rastering approach across a 4×4 micrometer region of the cell resulting in the whole cell spectrum containing measurements of scatter from the nucleus, cytoplasm and membrane. Subsequently the spectra are delivered to a classification algorithm which returns a probability that the patient will develop an adverse reaction to the radiotherapeutic treatment, and a probability that the patient will develop a full pathological response to the treatment, and a probability that the patient has high levels of radiosensitivity. The classification may be performed using supervised learning (support vector machines, naïve Bayes classifiers, neural networks, random forests, Fisher's linear discriminant analysis). In a preferred embodiment, this step of classification is performed using Principal Components Analysis Linear Discriminant Analysis.

The present invention will now be described more particularly with reference to the Examples and the drawings, in which are shown, by way of example only, a number of preferred embodiments of the present invention.

Accordingly, further aspects and advantages of the present invention will be disclosed in the following experimental section and are illustrative only and not limiting to the scope of the present application.

1. Example 1. Classification of Radiosensitivity in Lymphocytes from Prostate Cancer Patients 1.1. Cell Extraction, Culture and Irradiation This study comprised an analysis of blood lymphocytes from a total of 20 healthy volunteers and 20 prostate cancer patients. A total of 20 mls of blood was drawn from each volunteer and patient into lithium heparin tubes after obtaining informed consent from each of the donors. Peripheral blood mononuclear cells (PBMC) were isolated within 4 h of sample collection. A total of 6 ml of Dulbecco's modified phosphate buffered saline (DPBS) (Sigma) was added to 6 ml of heparinised blood, mixed by gentle inversion and overlaid over 15 ml of Histopaque. Samples were then centrifuged at 400 g for 30 min at room temperature. The PBMC layer was removed and washed three times. Finally, cells were centrifuged at 250 g for 5 minutes at room temperature. The cell pellet was then resuspended in 3 ml of full media (RPMI+12.5% (v/v) FBS+2 mML-glutamine (Sigma)) supplemented with 2.5% (v/v) phytohaemagglutinin (PAA Laboratories). One ml of cell suspension was transferred to a T25 flask containing 4 ml of full media. A total of 3 flasks were prepared for each donor and they were incubated for 72 hours at 37° C., 5% CO2 to allow separation of lymphocytes and monocytes by plastic adherence.

A total of 5 ml of cell suspension was placed in T25 flasks for irradiation. The flasks were either sham irradiated (0Gy) or irradiated (0.05Gy and 0.5Gy) 17 hours after plating using a cobalt 60 gamma ray teletherapy source at St. Luke's hospital, Dublin. The dose rate was approximately 1.5 Gy/min during these experiments and was determined from a decay corrected measurement of the in-beam axial dose at an 80 cm source to chamber distance (measured using a secondary standard ionization chamber within a water equivalent phantom). The dose settings that were used and the actual dose delivered, with their respective uncertainties, were 0.05Gy (0.058Gy±17%) and 0.5Gy (0.511Gy±2%). The actual dose that was delivered at the time of irradiation was determined from the axial dose, corrected for scatter and grid factors, the additional time that the sample was exposed to radiation ((with an accuracy of ±0.005 min) during the extension and recession of the source from the within the cobalt unit), and source to sample distance (191.5 cm for 0.05Gy and 100 cm for 0.5Gy). The samples were then placed in an incubator at 37° C. for 60 mins at which time, cells were fixed using 2% paraformaldehyde in phosphate-buffered saline. From the suspension, 40 µl was drop cast onto calcium fluoride ($CaF_2$) slides. The slides were then washed three times in deionised H2O and the samples were allowed to dry for Raman spectroscopic measurements.

1.2. Raman Spectroscopy

Raman spectroscopy was performed using a Horiba Jobin Yvon Labram HR800 UV system, equipped with a 660 nm solid-state diode laser delivering 100 mW of power to the sample. Spectra were acquired for each of the different donors over a period of 1 year. All samples (sham irradiated cells (0Gy) and irradiated samples (0.05Gy and 0.5Gy) from each individual were recorded on the same day, together with a spectrum of 1,4-Bis (2-methylstyryl) benzene and NIST SRM 2245 for calibration purposes. Multiple calibration spectra were recorded before recording a sequential group of cellular spectra. Spectra were recorded from 30-50 cells per dose and from each of the independent donors. The cells were ~8-12 µm in size and each spectrum was recorded from individual cells using a 4×4 µm raster scan of the cell including both signal from its nucleus and cytoplasm. Spectra were recorded with a 20 second integration time and averaged across three integrations per spectrum. Spectra were recorded using a diffraction grating ruled with 300 lines/mm giving a spectral resolution of ~2.1 cm$^{-1}$. The confocal hole was set to 150 µm with the grating centered at 1350 cm$^{-1}$. All spectra were recorded within two weeks of slide preparation. Slides were stored in a desiccator until measurement.

1.3. Raman Spectral Post Processing

Raman spectroscopy is a technique that requires rigorous pre- and post-processing procedures to be performed on the spectra to account for variations in performance of a Raman spectrometer from day to day and also to account for variations in instrument configuration from instrument to instrument. Some pre-processing steps include intensity and wavenumber calibration[18]. After spectral measurement, post-processing steps include baseline correction processes[19-21], removal of substrate background, filtering of noise[22], smoothing etc. All post-processing was performed in Matlab 2009b (The Mathworks Inc.) with the PLS Toolbox v. 7 and v. 8 (Eigenvector Research Inc.).

In the present Example, a spectral baseline subtraction employing a heavily smoothed spectrum as a baseline was used, which has been documented elsewhere[23-25,26]. Briefly, the method uses Savitsky Golay smoothing to smooth any given spectrum with a 4$^{th}$ order polynomial over a window size of 450 wavenumbers. The heavily smoothed spectrum is then subtracted from the original spectrum. Subsequently any residual baseline is removed by applying a rubberband baseline correction. The 'rubberband' function finds a set of local minima throughout the spectrum, stretches a linear segment of baseline between successive local minima and attaches the segments to both endpoints of the spectral window. The baseline is constrained to be always equal to or lower than the intensity of the spectrum so that no negative spectral intensities occur after subtraction. If the slope of the segment is not high enough for the segment of the baseline to touch the signal at the next local minimum then the slope is iteratively increased until it does[27]. This procedure was applied to the cellular spectra after the first baseline subtraction. Normalisation was then applied. Normalisation is a scaling process that is used in order that small changes in spectral variables can be detected[28]. In the present study unit vector normalisation was employed. A vector normalised spectrum is a spectrum whose vector length is unity and points in the direction of the original vector (each wavenumber is a vector with magnitude equal to the intensity at that wavenumber).

Outlier removal was then performed using a repeated Grubb's test for outliers. The test is performed by performing PCA on the entire data set, computing the Mahalanobis distances on the scores of principal components and ordering them in terms of largest to smallest. The most extreme values are considered outliers.

The remaining spectra were then fit by a series of spectra from reference compounds including DNA, RNA, various proteins and lipids, and carbohydrates, plus the spectrum of the $CaF_2$ slide upon which the cells were deposited. The fitting was performed using a non-negative-least-squares algorithm that constrained the fitting coefficient for each reference spectrum to positive values only. The estimated contributions of $CaF_2$ to each spectrum (in terms of the fitting coefficient) were subsequently removed from each cellular spectrum by subtraction of the product of the fitting coefficient with the reference spectrum of $CaF_2$.

1.4. Measurement of Radiosensitivity

In this study, the Patterson G2 chromosomal assay was performed as a measure of radiosensitivity. Thirty minutes after irradiation 0.2 ml of colcemid (10 µg/ml) (Sigma) was added to in-vitro cultured lymphocytes. Cells were incubated for 60 minutes and then centrifuged at 1400 rpm for 10 minutes. After centrifugation, cells were plunged in ice to cool rapidly. Supernatant was removed and replaced with 10 ml of pre-cooled 0.075M KCl. Cells were then vortexed and placed in ice for 20 minutes. After centrifugation at 1400 rpm for 10 minutes, cells were fixed with 3:1, methanol: glacial acetic acid. After a final centrifugation fixative was replaced with fresh fixative and stored at 4 degrees Celsius overnight or for longer if needed. Slides were prepared by rinsing in methanol 24 hours prior to use, and then briefly washed and kept in de-ionized water until use. One-to-two drops of the cell suspension were dropped onto the slides from a height and brought through a Bunsen burner to dry. Three percent Geimsa (GURRS) was used in pH 6.8 buffer to stain slides for 15 minutes. Slides were washed in pH 6.8 buffer and left to dry before mounted in DPX. Slides were left for 24 hours (minimum) before analysis. The mitotic inhibition, the number of cells in interphase relative to the number of cells in metaphase, was recorded for 1000 cells per slide. The number of chromosomal aberrations was recorded for 50 cells per slide and was multiplied by two to get a percentage of aberrations for each slide.

For each individual donor in both the healthy control and patient cohort, his/her radiation-induced G2 score was calculated. The radiation induced G2 score was calculated by subtracting the G2 scores in each individual's unirradiated control from his/her irradiated score at a dose of 0.5Gy. Radiosensitivity for both the healthy control and patient cohort was then defined by the 90$^{th}$ percentile of the radiation induced G2 score at 0.5Gy in the healthy control cohort. The 90$^{th}$ percentile of the radiation induced G2 score for healthy donors in this study was found to be 150. Both patients and healthy controls were therefore considered radiosensitive if their radiation induced G2 score at 0.5Gy was above this threshold.

1.5. Classification of Radiosensitivity

Three classification methods were used to classify lymphocyte spectra from normo-sensitive and radiosensitive individuals, including consensus Principal Component Analysis Linear Discriminant Analysis (PCA-LDA), a radial basis function (RBF) support vector machine (SVM) and a random forest classifier (RF). In the consensus PCA-LDA approach, each individual is assigned to a class on the basis of the majority of their lymphocyte spectra being assigned to one of the classes. A 10 fold CV repeated 10 times was performed for each classification of normo-sensitive individuals versus those classified as radiosensitive using spectra from their unirradiated (0Gy) lymphocytes. Only spectra from patients at their baseline (pre-treatment) were used for the classification. The resulting Matthews Correlation Coefficient (MCC, sensitivity, specificity, model complexity and optimised parameters for the repeated 10-fold CVs for each classification algorithm are shown in Table 1. In all instances the classification rates are relatively high with MCCs above 0.69. Standard deviations are provided to show the variation of the performance and complexity of the classifiers over the 10 epochs. The best classification performance resulted from the classification using the RBF-SVM with an MCC of 0.83 over the 10 repeats.

TABLE 1

MCC, Sensitivity and specificity of the classifications of normal versus radiosensitive individuals based on their radiation induced G2 score cut off of 150 chromosomal aberration per 1000 cells for 10 fold CV repeated 10 times using PCA-LDA, SVM's and RF's. Standard deviations are shown in brackets.

| Classifier | Complexity and parameter optimisation | MCC | Sensitivity | Specificity |
| --- | --- | --- | --- | --- |
| PCA/LDA | nLVs: 36 (1) | 0.69 (0.01) | 0.94 (0) | 0.73 (0) |
| RBF-SVM | C: 50,000 (0) Gamma: 20.33 (25.54) | 0.83 (0.095) | 0.94 (0.032) | 0.90 (0.058) |
| RF | Numbers of trees: 172 (175) Number of leaf nodes: 38 (19) | 0.71 (0.082) | 0.87 (0.035) | 0.93 (0.025) |

Due to the complexity of each of the models used to classify normo-sensitive versus radiosensitive individuals, the origin of classification is disclosed in this application in the form of difference spectra, statistical testing and band analysis. It is known that in PCA the main source of discrimination between spectral classes correlates strongly with the difference spectrum between the classes[29], and therefore this would be the source of discrimination in a consensus PCA-LDA classification algorithm. The difference spectrum is then a reference upon which the consensus PCA-LDA algorithm performs the discrimination between classes, and represents a spectral biomarker of radiosensitivity. The mean and difference spectra of normo-sensitive and radiosensitive individuals is provided in FIG. 1. Band analysis was performed on normo-sensitive versus radiosensitive individuals to assess the differences in spectral profiles in terms of both radiosensitivity and dose. FIG. 1 shows the band areas for several regions of the spectrum. These differences are seen to be slight but significant between the two cohorts, particularly at the control (0Gy) and at the 0.5Gy dose point.

Figure 3:
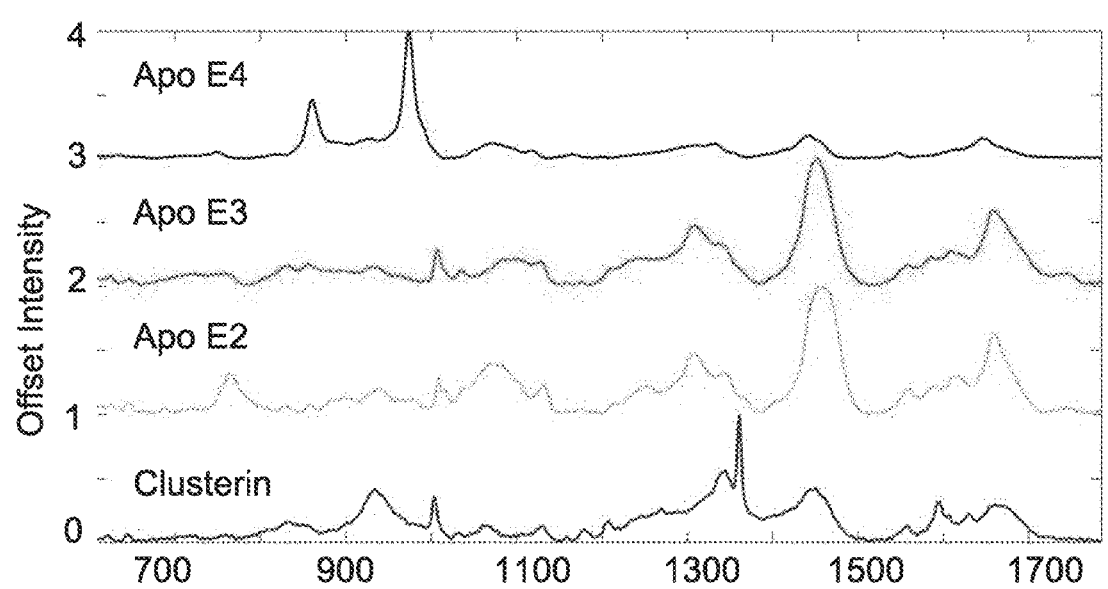
FIG. 3 shows the stacked Raman spectra of apolipoproteins ApoE4, ApoE3, ApoE2 and clusterin which illustrates the capability of Raman spectroscopy to discriminate between the spectrum of apolipoprotein E4 and its isoforms.

While the differences in spectral profiles between normo-sensitive and radiosensitive individuals are relatively small, the dose response associated with DNA and nucleic acids differ substantially. The bands associated with lipids and proteins are also only observed to differentiate following exposure to IR. In particular, the band in the region 970-980 cm$^{-1}$ was observed to be lower in radiosensitive cell lines when compared to normal cell lines. Cells irradiated with 0.5Gy also showed higher levels of the band associated with apolipoprotein E4 (Apo E4) in radiosensitive individuals when compared to normal individuals. Measurements of the spectra of lyophilized apolipoprotein E4 (ApoE4), two of its isoforms and apolipoprotein J are shown in FIG. 3. A clear differentiating band is seen in the ApoE4 spectrum centred at 974 cm$^{-1}$ (CH$_3$ and CCH bond in unsaturated hydrocarbons in proteins[30]) and 837 cm$^{-1}$ (the α-helix carbon backbone stretch in the molecule[31]). Apo E4 is an intermediate density lipoprotein which has been associated with many diseases including cardiovascular disease and Alzheimer's disease[32]. Apo E4 plays an important role in both lipid transport and neuronal repair. While Apo E4 has not been associated with intrinsic radiosensitivity, it has been demonstrated that exposure of the brain to both γ-radiation and $^{56}$Fe irradiation in mice with the Apo E4 allele resulted in increased risk of cognitive impairments following irradiation compared to mice with either the Apo E2 or E3 alleles[32-34].

2. Example 2. Classification of Patients with Chronic Radiotherapeutic Treatment Toxicity Using Raman Spectroscopy of Blood Components

2.1. Cell and Plasma Extraction

This study comprised an analysis of blood lymphocytes and plasma drawn from a total of 42 prostate cancer patients. These patients were followed after radiotherapeutic treatment for cancer and had urinary toxicity measured at 2 years or more post-treatment in accordance with the CTCAE v4.0 criteria. In this cohort, a total of 20 patients exhibited no urinary toxicity and were assigned Grade 0 or Grade 1 (G0/G1) on the toxicity scale, while the remaining 22 patients exhibited Grade 2 or higher toxicity on this scale (G2+). Blood was drawn from these patients, was processed, and lymphocyte and plasma spectra were acquired and processed according to the protocol in sections 1.1-1.3.

3.1. Classification of Patients by Treatment Toxicity

Spectra were classified using three approaches: a consensus PCA-LDA algorithm, a Random Forests algorithm and a Support Vector Machine (SVM). Each a patient is assigned to a class of G0/G1 (no toxicity) or G2+(toxicity) on the basis of the majority of their lymphocyte or plasma spectra being assigned to one of the classes. The performance of the algorithms using lymphocyte spectra is shown in Table 2, and visualized in FIG. 4. This demonstrates the high specificity or sensitivity of this approach in classifying patients on the basis of treatment toxicity using lymphocyte spectra.

TABLE 2A

Sensitivities and specificities on classification of patients by radiotherapeutic treatment toxicity using Raman spectra of their lymphocytes, which are cultured in-vitro and are irradiated with gamma-ray photon doses as shown.

| Model | Dose (Gy) | Accuracy | Sensitivity | Specificity |
|---|---|---|---|---|
| PCA-LDA | 0 | 0.91 | 1.00 | 0.86 |
|  | 0.05 | 0.88 | 0.89 | 0.86 |
|  | 0.5 | 0.84 | 0.88 | 0.83 |
| Random forest | 0 | 0.80 | 0.82 | 0.79 |
|  | 0.05 | 0.87 | 1.00 | 0.84 |
|  | 0.5 | 0.84 | 1.00 | 0.80 |
| RBF-SVM | 0 | 0.82 | 0.76 | 0.86 |
|  | 0.05 | 0.97 | 1.00 | 0.95 |
|  | 0.5 | 0.84 | 0.88 | 0.83 |

Figure 4A:
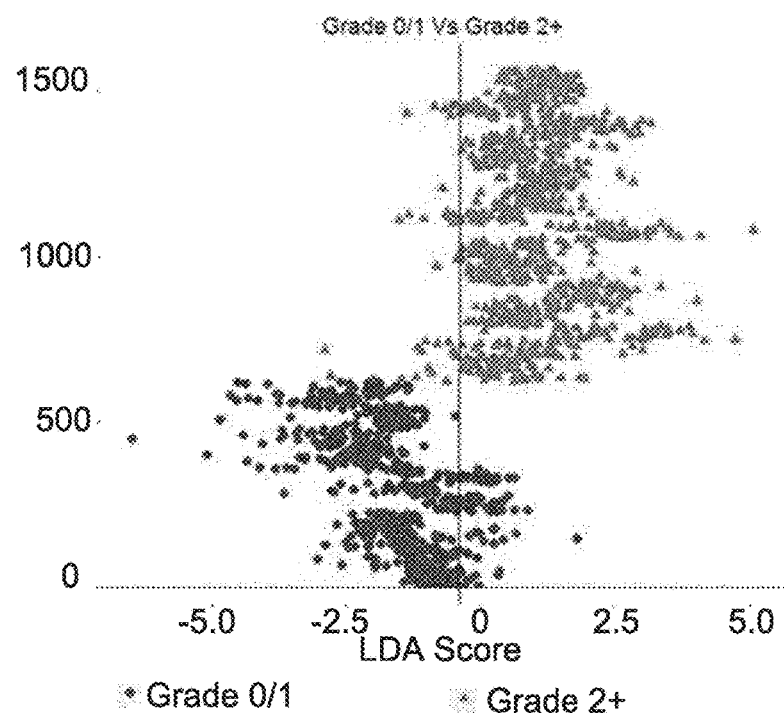
FIG. 4A visualizes the classification of patients on the basis of radiotherapeutic treatment toxicity on the basis of Raman spectra of their lymphocytes.
Figure 4B:
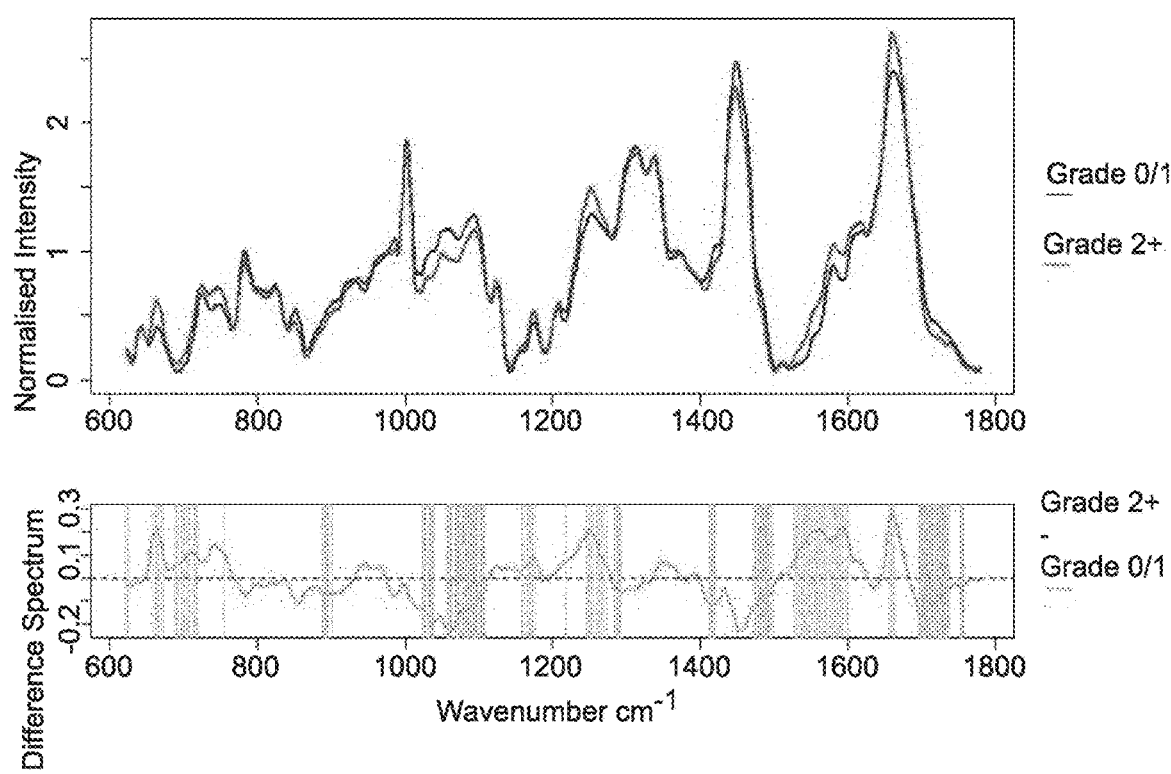
FIG. 4B visualizes the mean lymphocyte spectra of patients by treatment toxicity class, and the spectral biomarker which discriminates the classes. Shaded regions represent where the spectra of cells from patients with little to no toxicity were significantly higher (dark) or lower (light) than in patients with significant toxicity. Significance level is p<0.005.

The performance of the algorithms using lymphocyte spectra is shown in Table 2A, and visualized in FIG. 4A. This demonstrates the high specificity or sensitivity of this approach in classifying patients on the basis of treatment toxicity using lymphocyte spectra. In addition the data shows that it is possible to classify patients by treatment toxicity with or without a challenge dose of radiation in-vitro. In addition the spectroscopic biomarker displayed in FIG. 4B (bottom) represents the discriminating Raman spectral biomarker for toxicity in lymphocytes.

Figure 4C:
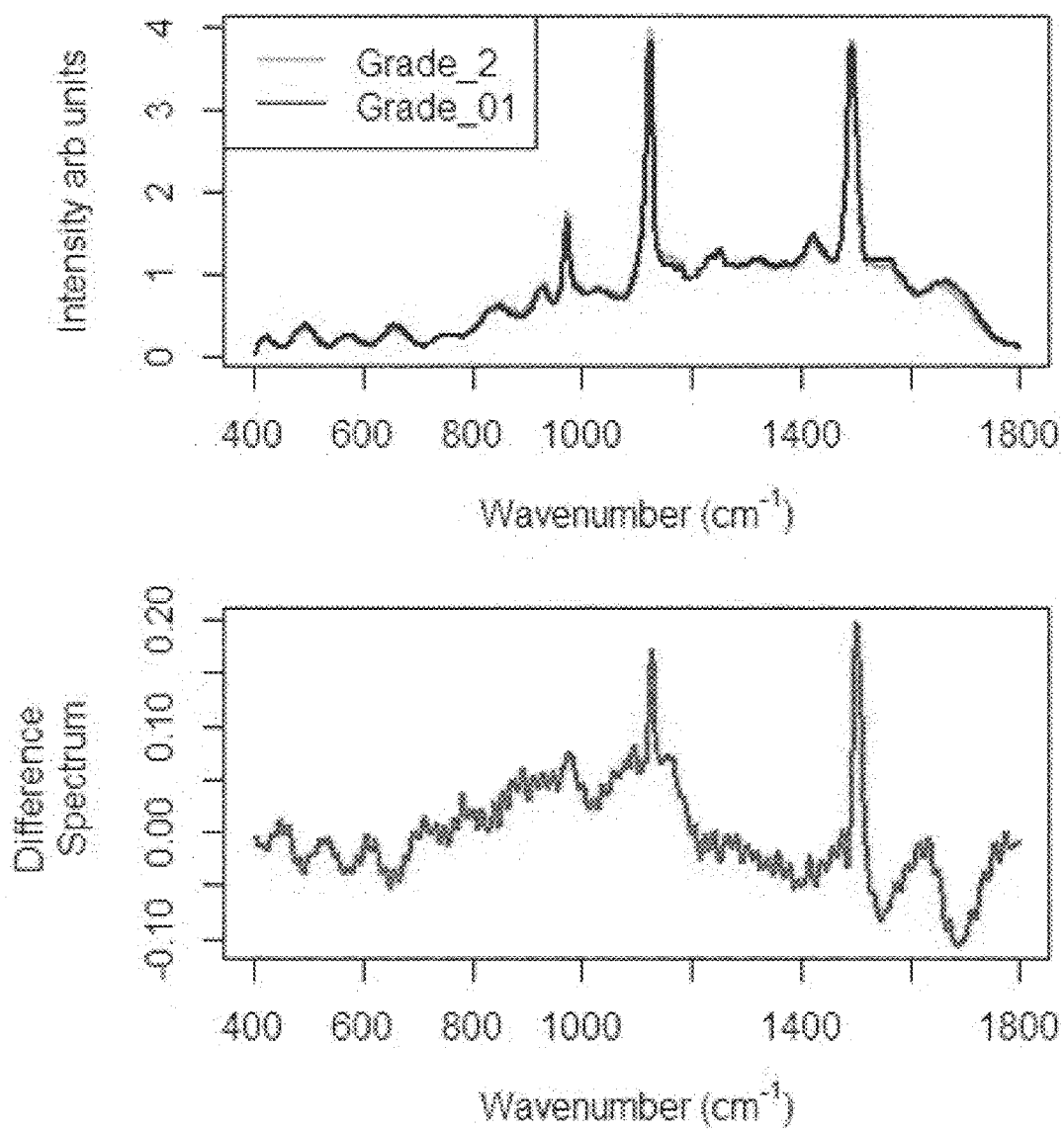
FIG. 4C visualizes the mean plasma spectra for patients by treatment toxicity class, and the spectral biomarker which discriminates the classes. This is for spectra measured at a 532 nm excitation.
Figure 4D:
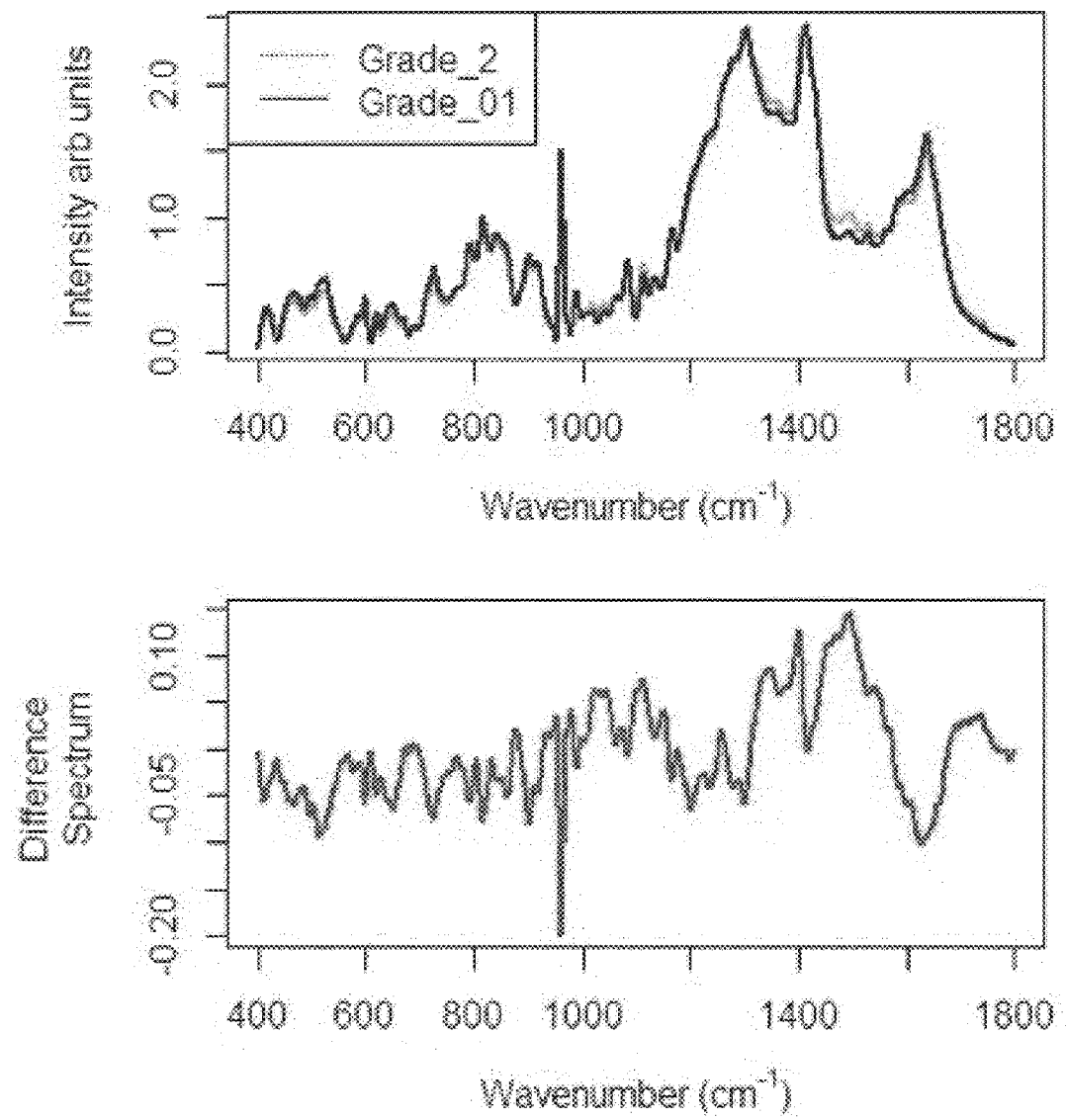
FIG. 4D visualizes the mean plasma spectra for patients by treatment toxicity class, and the spectral biomarker which discriminates the classes. This is for spectra measured at a 785 nm excitation.

Table 2B depicts the performance of two algorithms for classification of treatment toxicity based on the Raman spectra of plasma in these patients. Again, both algorithms are consensus algorithms where patients are assigned a class based on the majority of their spectra being in the class. Spectra in this instance were acquired with all settings as described previously, but in this case 10 spectra were taken from random positions within the sample using an excitation of either 532 nm or 785 nm, and with the sample deposited on glass substrates. FIGS. 4C (bottom) and 4D (bottom) depict the discriminating Raman spectral biomarker for toxicity in plasma at, respectively, 532 nm and 785 nm.

TABLE 2B

Sensitivities and specificities on classification of patients by radiotherapeutic treatment toxicity using Raman spectra of their blood plasma.

| Model | Sensitivity | Specificity |
|---|---|---|
| PCA-LDA | 0.77 | 0.73 |
| PCA-QDA | 0.81 | 0.78 |

3. Example 3. In-Vitro LCL Model of Extreme Radiosensitivity Analysed with Raman Spectroscopy

3.1. Cell Culture, Sample Preparation and Raman Spectroscopy

Ataxia Telangiectasia is a genetic disorder resulting from a deficiency in the action or regulation of the gene Ataxia Telangiectasia Mutated (ATM). Non-Hodgkin's lymphomas are radiosensitive tumours of the blood that have been associated with deficiency in the repair of DNA damage through the ATM pathways[35,36]. Turner Syndrome is a female condition whereby the individual is partly or completely lacking an X chromosome. Few studies have been performed on cells derived from individuals suffering from Turner syndrome in the field of IR, however some studies have found evidence that show individuals suffering from Turner syndrome exhibit increased levels of chromosomal aberrations following IR, resulting in increased radiosensitivity[37,38]. Immortalized lymphoblastoid cell lines derived from normal individuals and patients suffering from Ataxia Telangiectasia (AT), Turner Syndrome and AT plus non-Hodgkin's Lymphoma (AT-NHL) were used as a cellular model of radiosensitivity.

3.2. Culturing and Measurement of Radiosensitivity of LCL Lines

The 2139 (Turner Syndrome) and 2145 (Normal) cell lines are B-lymphocytes from normal individuals targeted and immortalised with the Epstein Barr virus and were obtained from Dr. Janet Hall at the Institut Curie, Paris, France. The AT2Bi (AT) and AT3Bi cell lines (AT NHL) are B-lymphocytes derived from two AT patients; both AT cell lines were targeted and immortalised with Epstein Barr virus and were obtained as a gift from Professor Malcolm Turner at the University of Birmingham. Over the course of this work, incidental findings showed that 2139 cells were lacking in an X chromosome and were diagnosed as having Turner syndrome and AT3Bi cells were found to have non-Hodgkins lymphoma in addition to AT deficiency.

Cells were cultured in full media (RPMI+12.5% (v/v) FBS+2 mML-glutamine) and were irradiated, and prepared for Raman spectroscopy as described earlier. Spectra were also acquired and pre-processed as described earlier.

Radiosensitivity for each cell line was measured using the G2 chromosomal aberration assay. This assay was performed for all doses and the radiation induced G2 score is provided in FIG. 5. Significance testing with a t-test was performed for each cell line compared to the normal cell line at each dose. No significant difference was observed between each cell line and the normal cell line at 0.05Gy or 2Gy. Both AT NHL and Turner syndrome cell lines were found to have a significantly higher radiation induced G2 score from the normal cell line at the 0.5Gy dose (p<0.05).

3.3. Classification of Raman Spectra of Radiosensitive Syndromes Using PCA-LDA

Four way classifications were performed on all cell lines simultaneously. Classifiers were either built with unirradiated spectra or irradiated spectra (0.05Gy or 0.5Gy) independently and only used spectra at 1 hour following IR. The number of latent variables used in each of the classifications was optimized using a leave one out CV, where the optimum number of latent variables was chosen from the models which resulted in maximum accuracy on testing. The accuracies, sensitivities, and specificities for classification of each of the classes are provided in Table 3, together with the optimized number of latent variables. The best performing model was the model built with spectra from unirradiated (control, 0Gy) spectra, with an overall accuracy of 0.87. While the performance of each of the models is relatively good, large numbers of latent variables were required for each of the classifications resulting in highly complex models, but which possessed no evidence of over fitting.

TABLE 3

Accuracies sensitivities and specificities for the 4-way classification of normal, AT, AT NHL and Turner syndrome cells. Model complexity is given by the number of latent variables (nLVs) chosen by the 10 fold cross validation optimization.

|  |  |  |  | Normal | AT | AT NHL | Turner Syndrome |
|---|---|---|---|---|---|---|---|
| 0 Gy | Accuracy | 0.87 | Sensitivity | 0.94 | 0.84 | 0.87 | 0.91 |
|  | nLVs | 42 | Specificity | 0.91 | 0.93 | 0.93 | 0.91 |
| 0.05 Gy | Accuracy | 0.76 | Sensitivity | 0.96 | 0.65 | 0.83 | 0.71 |
|  | nLVs | 28 | Specificity | 0.77 | 0.89 | 0.77 | 0.89 |
| 0.5 Gy | Accuracy | 0.81 | Sensitivity | 0.90 | 0.73 | 0.92 | 0.75 |
|  | nLVs | 49 | Specificity | 0.82 | 0.93 | 0.79 | 0.94 |

Two way classifications of normal versus AT, normal versus Turner syndrome and AT versus AT NHL spectra were also performed using a leave one out CV. All classifications were performed with spectra from unirradiated (control) cells as a result of the outcome of the 4-way classification. Discriminant analysis scores and probability distribution functions are plotted for each classification in FIG. 6 to provide a visual aid to illustrate classification performance. Accuracies, MCC's, sensitivities, specificities are provided in Table 4 along with the number of latent variables required in each of the classifications.

TABLE 4

Accuracies, MCC's, sensitivity and specificity for the classifications of Normal versus AT cells, AT versus AT with NHL, and normal versus Turner syndrome cells using control spectra.

|  | nLVs | Accuracy | MCC | Sensitivity | Specificity |
|---|---|---|---|---|---|
| Normal V AT | 28 | 0.94 | 0.88 | 0.93 | 0.95 |
| AT V AT NHL | 33 | 0.98 | 0.87 | 0.89 | 0.98 |
| Normal V Turner | 41 | 0.93 | 0.96 | 0.98 | 0.98 |

The number of latent variables was determined as described earlier with the exception that the optimum number of latent variables was chosen when the MCC of the test set was found to be at maximum.

All classifications resulted in an accuracy of 0.93 or greater. This shows the capability of Raman spectroscopy to discriminate between normal and radiosensitive cell phenotypes. In addition it demonstrates that distinct radiosensitive phenotypes can be discriminated within a mixed population (4-way classification) or within a paired (2-way) classification. These classifications can be performed using lymphocytes without the need for a priming (or challenging) dose such as that required in the G2 chromosomal aberration assay. While the classification performance was relatively good in both the four way classifications and the two way classifications, the numbers of latent variables required for each of the classifications resulted in highly complex models, but with no evidence of overfitting. For this reason interpretation of the classifications of each of the cell lines is performed using difference spectra and statistical tests to identify bands that were significantly different between normal and radiosensitive cell types. The difference in performance and complexity of the two way and four way classifications may be due to the subtle differences in the bands associated with the different types of radiosensitivity and their associated phenotypes.

3.4. Analysis of Difference Spectra of Radiosensitive Phenotypes Relative to Normal Cell Line The mean spectrum of control (0Gy) normal cell lines is provided in the top panel of FIG. 7. The difference spectrum of normal and all other cell types are provided in the bottom three panels of FIG. 7. Dark and light shaded regions represent where the regions of the spectra of each cell type were found to be significantly higher or lower than the normal cell lines respectively. Students t-tests were performed using a 2 tailed t-test for a significance level of p<0.005. Similarities exist in the profile of the difference spectra for each condition with, in particular, decreases in the region's 750-790 cm$^{-1}$ (associated with tryptophan[39], DNA/RNA[40], phosphatidylinositol, phosphatidylethanolamine[41]), 1110-1200 cm$^{-1}$ (C—N and C—C stretching of proteins and lipids[42,43], Carbohydrates and nucleic acids[44]), 1230-1270 cm$^{-1}$ (Amide III[45], RNA, Guanine and cytosine[44]), and 1580-1650 cm$^{-1}$ (C=N and C=C stretching in quinoid rings[46], Amide I[47]) and increases in the regions 1050-1100 cm$^{-1}$ (PO$_2^-$ stretching in DNA[48], phospholipids[42], triglycerides), 1290-1330 cm$^{-1}$ (CH$_2$ deformation[49], triglycerides, Amide III[48]) and 1660-1680 cm$^{-1}$ (Amide I[43], cholesterol ester[41]).

Both AT cell lines exhibit very similar spectral differences relative to normal cells. These differences are, however, more intense in AT NHL versus AT cells in the region 660-690 cm$^{-1}$ (tyrosine[39], ring breathing modes of DNA[48]), while increases were only observed in the regions 810-880 cm$^{-1}$ (phosphodiester bands in DNA/RNA[39,40], polysaccharides[50]), 1030-1050 cm$^{-1}$ (carbohydrates[45], proline and phenylalanine[43,51]), 1340-1360 cm$^{-1}$ (Guanine[40], tryptophan[43]), 1450-1470 cm$^{-1}$ (CH$_2$CH$_3$ deformation[52], nucleic acids[53]), and 1700-1800 cm$^{-1}$ (=O lipids[42], Ester groups[41]) in AT NHL cells when compared to AT cells. As these differences are only seen in AT NHL cells they may be considered together as spectral biomarkers differentiating NHL from AT radiosensitivity.

Some similarities were also observed in the difference spectra of AT NHL, and Turner syndrome cells. Decreases were observed in the regions 920-950 cm$^{-1}$ (C—C stretching of proline[43], polysaccharides) and 1350-1370 cm$^{-1}$ (tryptophan[43], guanine[39], lipids[39]) and were only observed in the difference spectra of AT NHL and Turner syndrome cells. Turner syndrome exhibits distinct differences in the two regions of the spectrum compared to all other conditions; decreases in spectral intensity were observed in a long band in the region of 850-950 cm$^{-1}$ (proline[43], RNA[48], proteins and polysaccharides) and an increase in a sharp double peak in the region 1410-1440 cm$^{-1}$ (Guanine and adenine[40], CH$_2$ deformation in lipids[39]) which may be spectral biomarkers differentiating Turner Syndrome from AT radiosensitivity and NHL.

Again the single band located in the region from 960-985 cm$^{-1}$ was observed to be decreased in both AT cell lines but not in the Turner Syndrome cell line. This band is tentatively assigned to apolipoprotein E4. This suggests that detection of substantial alterations in the spectral intensity of bands associated with ApoE4 may be used as a means of detection of radiosensitivity and may represent a spectral biomarker for ATM deficiency.

3. Example 3. Prediction of Tumour Regression Grade in Oesophageal Cancer Patients

3.1. Tissue Preparation

Tissue was obtained from patients suspected of cancer of the oesophagus and colon/rectum prior to administration of neo-adjuvant chemoradiotherapy for debulking of the tumour volume prior to its surgical excision. After neo-adjuvant chemoradiotherapy the tumour regression as a result of the therapy was graded according to a 5 point scale termed the 'tumour regression grade' or TRG score where 1 represents complete regression, 2 represents a partial regression, 3 is an intermediate regression and 4 and 5 represent slight to no regression.

The tissue was preserved in a standard manner through fixation in 4% formalin solution and subsequently embedded in paraffin wax. A 10 μm thick section of the tissue was cut from each patient tissue block using a microtome and the tissue was mounted on a 2.5 mm thick calcium fluoride (CaF$_2$) slide for spectroscopy. A parallel 4 μm thick section was also cut a stained with haemotoxylin & eosin (H+E) for reference purposes during spectroscopic histopathological imaging. The tissue for spectroscopic imaging was subsequently chemically dewaxed according to a protocol developed previously[49]. Oesophageal cancer tissues from 38 patients who had provided their full consent were used in this work.

3.2. Raman Spectroscopy and Spectral Pre-Processing

Raman spectroscopy was performed, as described earlier, using a Horiba Jobin Yvon Labram HR800 UV system, equipped with a 660 nm solid-state diode laser delivering 100 mW of power to the sample. Spectra were acquired in point measurement mode using a ×100 objective and a diffraction grating ruled with 300 lines/mm giving a spectral resolution of ~2.1 cm$^{-1}$. The confocal hole was set to 150 μm with the grating centered at 1350 cm$^{-1}$. Slides were stored in a desiccator until measurement. Each individual tissue spectrum was measured with a 20 second integration time averaged over 3 simultaneous measurements. In addition a calibration spectrum of 1,4-Bis (2-methylstyryl) benzene and NIST SRM 2245 were taken twice daily for spectral calibration in post-processing. A total of 100 spectra were recorded separately from both the stroma and epithelial portions of the tissue from each patient using the parallel H+E stained section as a reference.

All post processing was performed using Matlab version 8.5 (R2015a; Mathworks, USA) using the PLS-Toolbox version 7.9.5 (Eigenvector Research Inc.) and in-house algorithms. All tissue spectra were initially calibrated and baseline corrected as described previously with the background spectrum of CaF$_2$ removed by subtraction. Each spectrum was then vector normalized.

3.3. Classification of TRG Status

All spectra were incorporated into the classification algorithm without further fitting or pre-processing. The dimensionality of the spectra was first reduced using principal components analysis and the spectra were then classified by TRG status using a quadratic discriminant analysis (QDA) algorithm. As there is some overlap between intermediate TRG score grades, to develop and test the algorithm the spectra were collapsed into new classes as follows. In the first, a 2-class distribution was created where patients with TRG scores of 1 and 2 were collapsed into one class (class 1) and patients with TRG scores of 3 and 4 were collapsed into another (class 2). This represents a clinical situation where patients are being distinguished on either complete to partial regression (class 1) versus slight to no regression (class 2). In the second class distribution patients with TRG scores of 1 and 4 remained in a separate class and those with TRG scores of 2 and 3 were combined into a third class. This represents a clinical situation where patients are discriminated into three classes and are distinguished on complete regression (TRG 1), partial to slight regression (TRG 2 and 3) and no regression (TRG 4). In the final class distribution a four way classification of patients into their original TRG score classes was performed.

The performance of the algorithm was determined using a repeated hold-out approach with spectra from 80% of the patients used to develop the classification algorithm and 20% to test it at each epoch. This process was performed a total of 20 times and the performance of the PCA-QDA algorithm in predicting the TRG status of a patient at the test phase was expressed as a mean of the sensitivities and specificities outputted by the algorithm over the 20 individual executions of its validation. The mean performances of the algorithm for two way, three-way and four-way classification of the TRG status of a test patient are shown in tables 5 and 6. Table 5 shows the performance of the algorithm in classifying on the basis of the spectra from epithelial cells, and Table 6 the performance of the algorithm in classifying on the basis of spectra from stromal cells.

TABLE 5

Sensitivities and specificities for classification of TRG status using spectra of epithelial cells

|         | Sensitivity | Specificity |
|---------|-------------|-------------|
| 2 Class | 0.92        | 0.84        |
| 3 Class | 0.95        | 0.94        |
| 4 Class | 0.97        | 0.97        |

TABLE 6

Sensitivities and specificities for classification of TRG status using spectra of stromal cells

|         | Sensitivity | Specificity |
|---------|-------------|-------------|
| 2 Class | 0.93        | 0.87        |
| 3 Class | 0.97        | 0.91        |
| 4 Class | 0.98        | 0.99        |

It is clear that the use of spectra from stromal cells produces an algorithm which slightly outperforms the classification algorithm which uses spectra from epithelial cells, and is particularly good in classifying spectra from patients on the basis of their TRG status rather than any of the collapsed class distributions as outlined earlier. Each of the models used the first 12 principal components in developing the classification hyperplane.

Figure 8A:
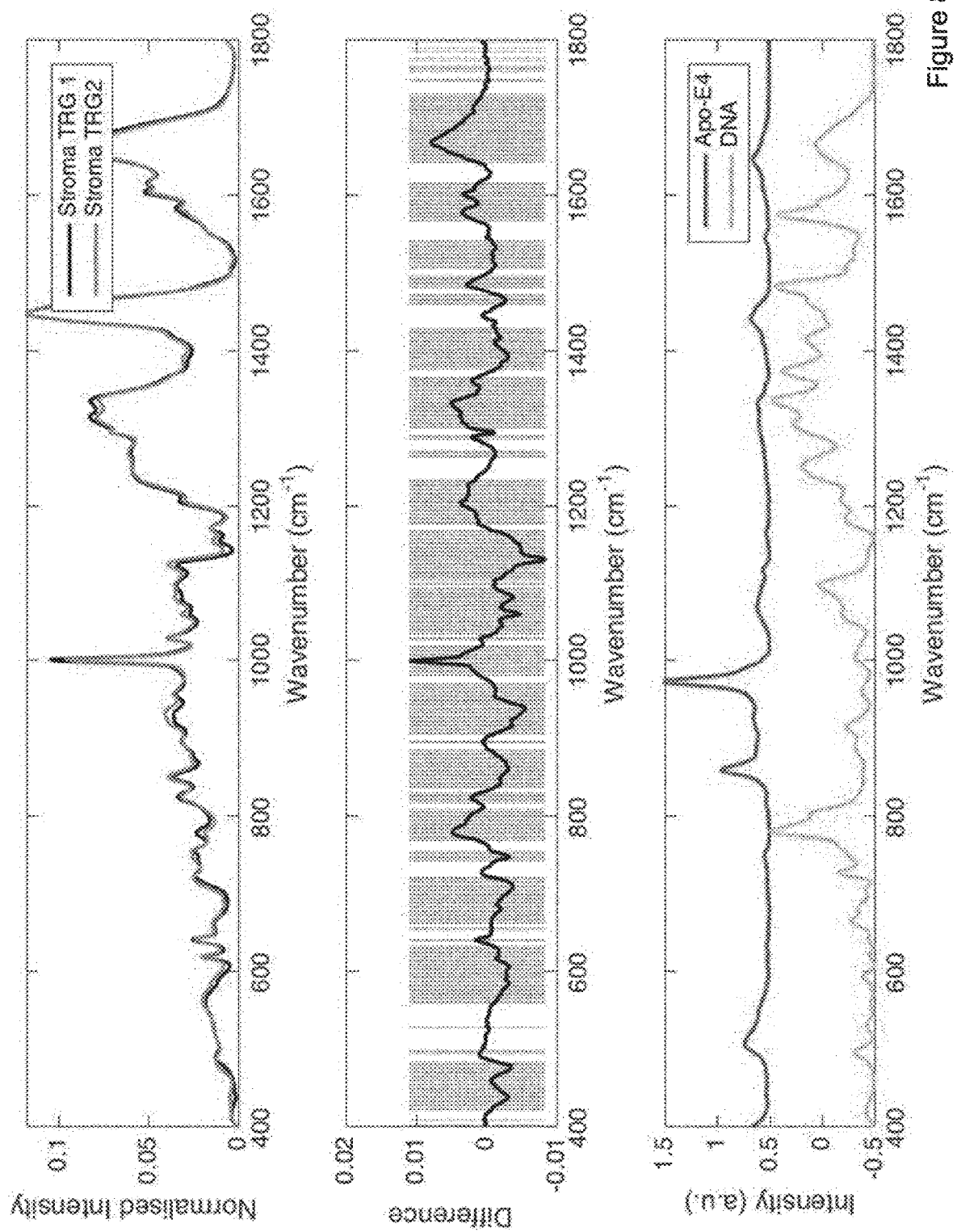
FIG. 8A shows the mean spectra of stromal tissue (top panel), difference spectra between the mean spectra of stroma of patients with a TRG score of 1 versus those with a TRG score of 2 (middle panel) and reference spectra (bottom panel)
Figure 8B:
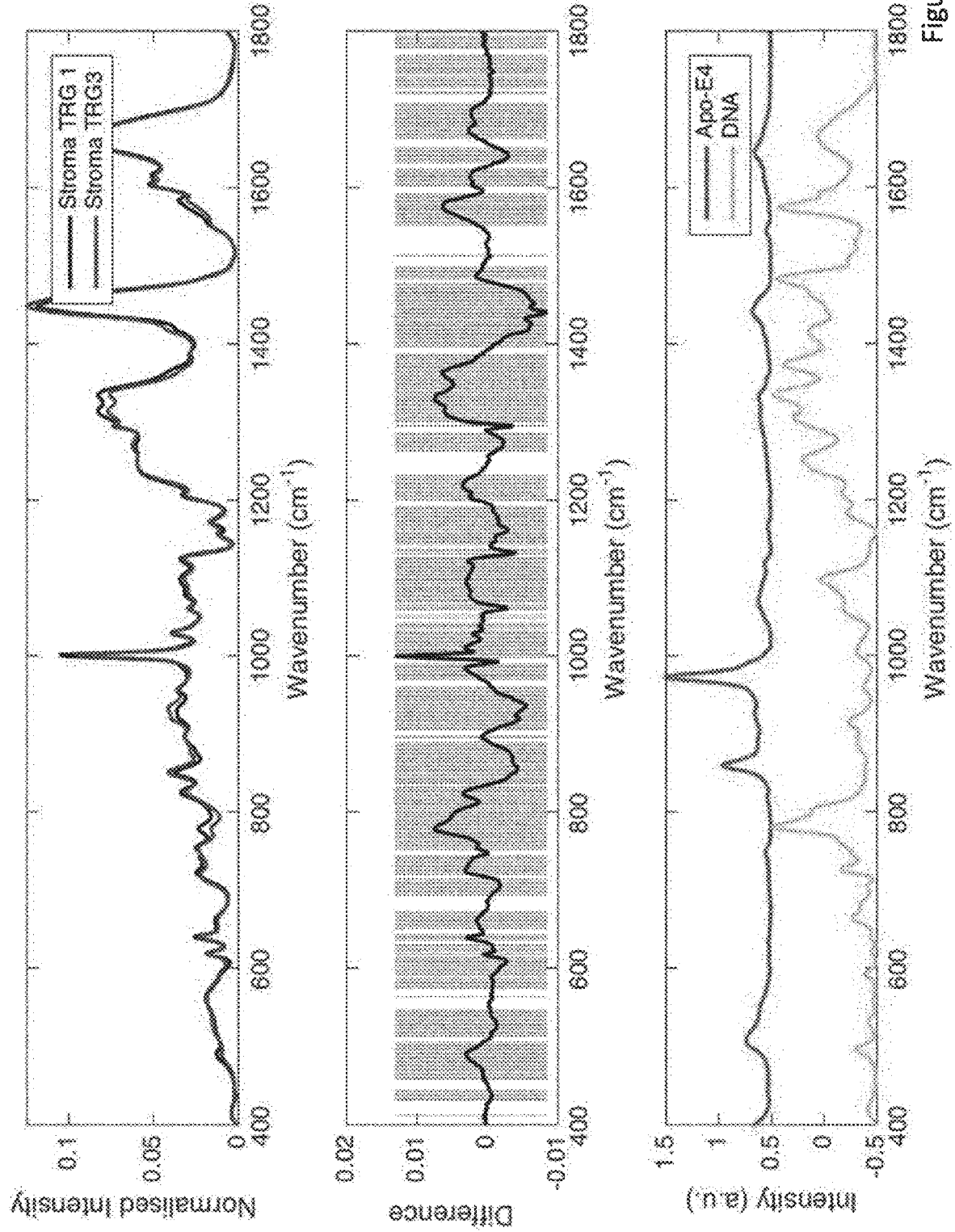
FIG. 8B shows the mean spectra of stromal tissue (top panel), difference spectra between the mean spectra of stroma of patients with a TRG score of 1 versus those with a TRG score of 3 (middle panel) and reference spectra (bottom panel)
Figure 8C:
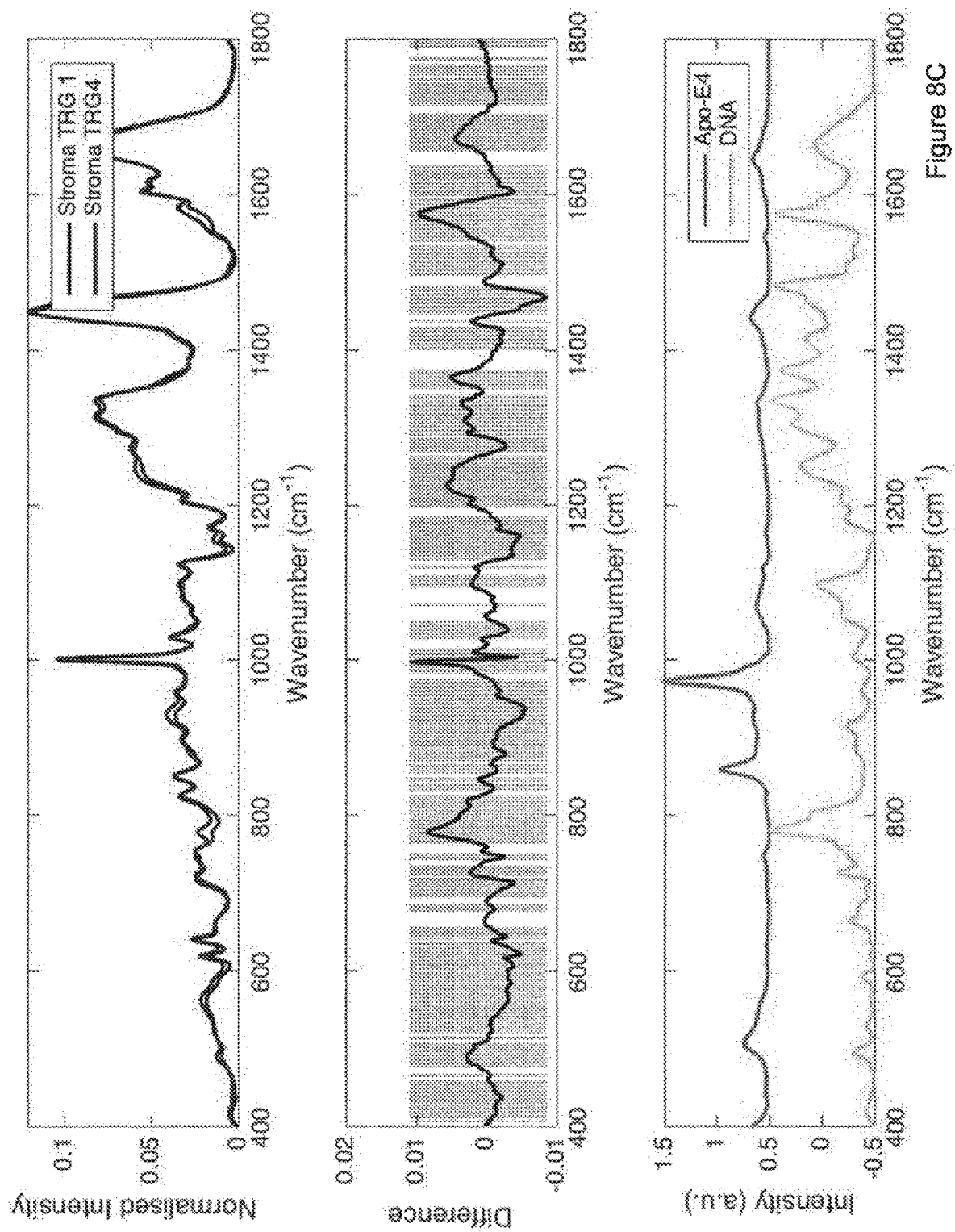
FIG. 8C shows the mean spectra of stromal tissue (top panel), difference spectra between the mean spectra of stroma of patients with a TRG score of 1 versus those with a TRG score of 4 (middle panel) and reference spectra (bottom panel)

In an attempt to elucidate the spectral origin of this classification, FIG. 8 shows the difference spectra between the stroma from patients with scores of TRG 1 relative to those with TRG score of 2 (FIG. 8(a)), TRG score of 3 (FIG. 8(b)) and TRG score of 4 (FIG. 8(c)). In each case the difference spectra are representative of the spectral biomarker discriminating the spectra of stroma in patients with a TRG score of 1 from those with a TRG score higher than this. In each subplot are plotted the mean spectra of the spectra from each class (top panel), the difference spectrum (middle panel) together with shaded regions found to be significantly different using a two-tailed students t-test ($p<0.005$), and spectra of apolipoprotein E4 (Apo-E4) and DNA for reference purposes (bottom panel). In each difference spectrum a multitude of bands are seen to change intensity, although some of the most prominent ones are those associated with the backbone of the DNA molecule (centred near 780 $cm^{-1}$) and those associated with the strong modes of vibrations of Apo-E4 (near 860 $cm^{-1}$ and 970 $cm^{-1}$). It is seen that the overall intensity of the vibration of the DNA backbone increases while that of the Apo-E4 bands decreases as TRG score increases. This suggests potential increases in metabolic activity in the stromal cells and decreased potential to abrogate oxidative stress as a key factor that discriminates patients on the basis of their response to adjuvant chemo-radiotherapy.

Figure 9:
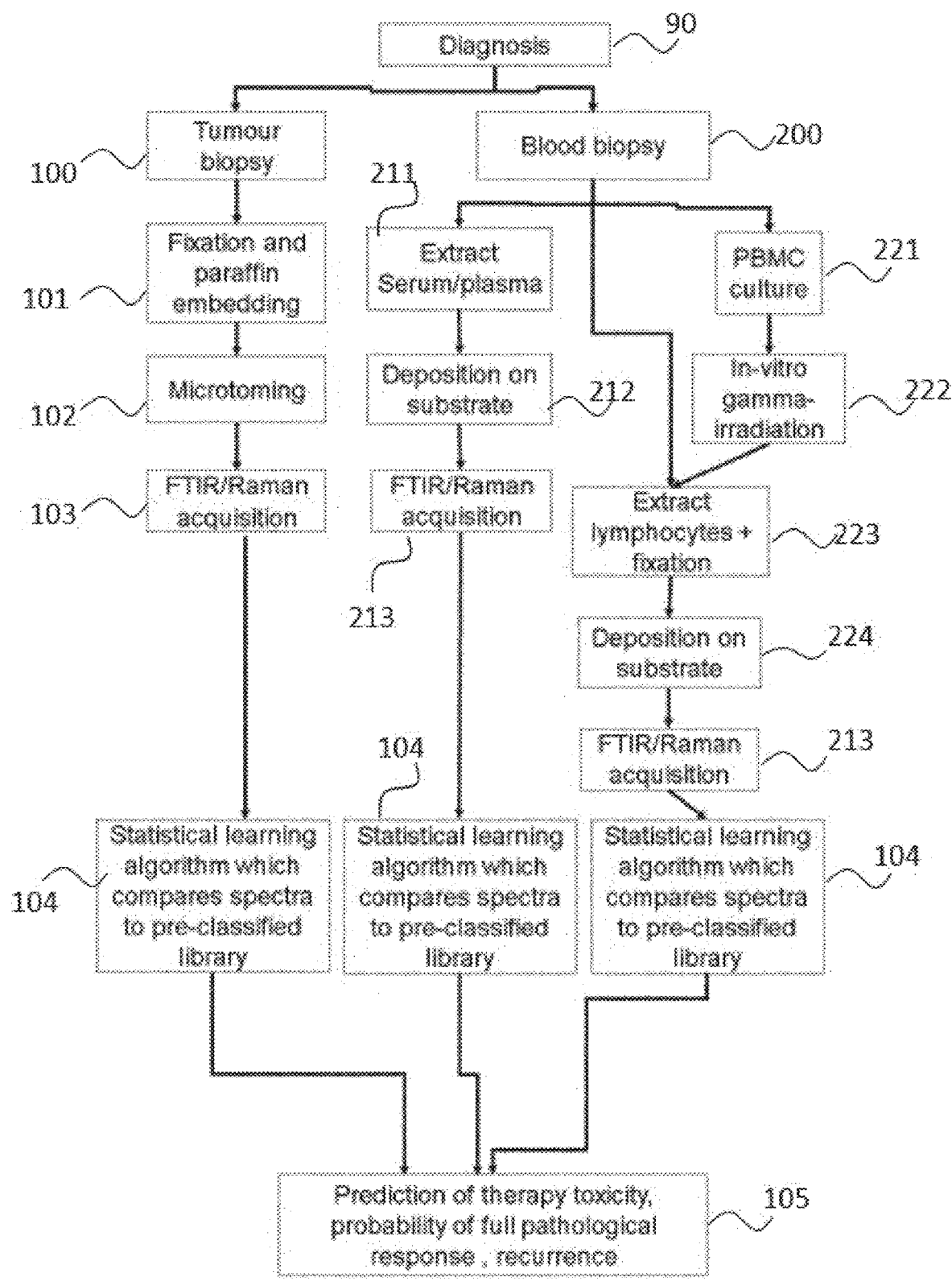
FIG. 9 is a flowchart of the steps of the prognostic method of the present invention.

FIG. 9 is a flow chart depicting the steps of the prognostic method of the present invention, showing the steps for tumour or tissue biopsy; and the steps for blood extracts such as serum or plasma.

In cases where the cancer is a solid tumour and a biopsy of the tumour can been taken from the patient, the following biopsy and imaging method may be used. The steps comprise:

obtaining diagnosis 90 of a cancer patient;
obtaining sample via tumour biopsy 100;
subjecting sample to fixation and paraffin embedding 101;
performing microtoming on sample 102;
acquiring FTIR/Raman spectra 103;
analysing obtained images by a statistical learning algorithm which compares obtained spectra to spectra from a pre-classified library 104; and
predicting response to therapy 105.

Step 103 may comprise acquiring FTIR or Raman imaging of the sample. This acquisition step may comprise obtaining spectra from many points in the sample. The Acquisition step (imaging) may comprise histological analysis and selection of a point or group of points on the sample from which the vibrational spectra will be analysed in later steps.

In cases where a blood sample is taken from a patient, the blood sample may be used whole and analysed or the plasma may be extracted and analysed or the lymphocytes may be extracted and analysed.

The steps for analysing plasma are as follows:
obtaining 90 diagnosis of a cancer patient;
obtaining 200 blood sample;
extracting 211 serum or plasma;
depositing 212 serum or plasma on substrate;
acquiring 213 Raman/FTIR spectra;
analysing 104 obtained spectra by a statistical learning algorithm which compares obtained spectra to spectra from a pre-classified library; and
predicting 105 response to therapy.

The steps for analysing lymphocytes are as follows:
obtaining 90 diagnosis of a cancer patient;
obtaining 200 blood sample;
isolating 221 peripheral blood mononuclear cells (PBMC);
subjecting 222 whole blood sample to in-vitro gamma-irradiation;
extracting 223 lymphocytes;
fixing 224 lymphocytes;
depositing 225 fixed lymphocytes on substrate;
acquiring 213 Raman/FTIR spectra;
analysing 104 obtained spectra by a statistical learning algorithm which compares obtained spectra to spectra from a pre-classified library; and
predicting 105 response to therapy.

Step 221, in which the peripheral blood mononuclear cells such as lymphocytes and monocytes are isolated from the sample is optional. Other blood components may be present during analysis.

Step 222, in which the lymphocytes are given a challenge dose of gamma radiation is optional. The lymphocytes may be analysed without in-vitro gamma-irradiation.

BIBLIOGRAPHY

1. Lievens, Y. & Grau, C. Health economics in radiation oncology: introducing the ESTRO HERO project. *Radiother. Oncol.* 103, 109-12 (2012).
2. Rosenblatt, E. et al. Radiotherapy capacity in European countries: an analysis of the Directory of Radiotherapy Centres (DIRAC) database. *Lancet. Oncol.* 14, e79-86 (2013).
3. Reynolds, J. V. et al. Long-term outcomes following neoadjuvant chemoradiotherapy for esophageal cancer. *Ann. Surg.* 245, 707-16 (2007).
4. Thompson, A. M. & Moulder-Thompson, S. L. Neoadjuvant treatment of breast cancer. *Ann. Oncol.* 23 Suppl 1, x231-6 (2012).
5. Ludwig, J. A. & Weinstein, J. N. Biomarkers in cancer staging, prognosis and treatment selection. *Nat. Rev. Cancer* 5, 845-56 (2005).
6. Bibault, J.-E. et al. Personalized radiation therapy and biomarker-driven treatment strategies: a systematic review. *Cancer Metastasis Rev.* 32, 479-92 (2013).
7. Krause, D. S. & Van Etten, R. A. Tyrosine kinases as targets for cancer therapy. *N. Engl. J. Med.* 353, 172-87 (2005).
8. van't Veer, L. J. & Bernards, R. Enabling personalized cancer medicine through analysis of gene-expression patterns. *Nature* 452, 564-70 (2008).
9. van de Vijver, M. J. et al. A gene-expression signature as a predictor of survival in breast cancer. *N. Engl. J. Med.* 347, 1999-2009 (2002).
10. Rosell, R., Bivona, T. G. & Karachaliou, N. Genetics and biomarkers in personalisation of lung cancer treatment. *Lancet* 382, 720-31 (2013).
11. Mulrane, L., Rexhepaj, E., Penney, S., Callanan, J. J. & Gallagher, W. M. Automated image analysis in histopathology: a valuable tool in medical diagnostics. *Expert Rev. Mol. Diagn.* 8, 707-25 (2008).
12. Brennan, D. J., O'Connor, D. P., Rexhepaj, E., Ponten, F. & Gallagher, W. M. Antibody-based proteomics: fast-tracking molecular diagnostics in oncology. *Nat. Rev. Cancer* 10, 605-17 (2010).
13. Klein, M. E. et al. Prediction of the Oncotype DX recurrence score: use of pathology-generated equations derived by linear regression analysis. *Mod. Pathol.* 26, 658-64 (2013).
14. Kraus, J. A., Dabbs, D. J., Beriwal, S. & Bhargava, R. Semi-quantitative immunohistochemical assay versus oncotype DX(®) qRT-PCR assay for estrogen and progesterone receptors: an independent quality assurance study. *Mod. Pathol.* 25, 869-76 (2012).
15. Wistuba, I. I., Gelovani, J. G., Jacoby, J. J., Davis, S. E. & Herbst, R. S. Methodological and practical challenges for personalized cancer therapies. *Nat Rev Clin Oncol* 8, 135-141 (2011).
16. Haibe-Kains, B. et al. Inconsistency in large pharmacogenomic studies. *Nature* 504, 389-393 (2013).
17. Huber, F. et al. Comprehensive validation of published immunohistochemical prognostic biomarkers of prostate cancer-what has gone wrong? A blueprint for the way forward in biomarker studies. *Br. J. Cancer* 112, 140-8 (2015).
18. Berg, R. W. & Nerbygaard, T. Wavenumber Calibration of CCD Detector Raman Spectrometers Controlled by a Sinus Arm Drive. *Appl. Spectrosc. Rev.* 41, 165-183 (2006).
19. Mazet, V., Carteret, C., Brie, D., Idier, J. & Humbert, B. Background removal from spectra by designing and minimising a non-quadratic cost function. *Chemom. Intell. Lab. Syst.* 76, 121-133 (2005).
20. Baker, M. J. et al. Using Fourier transform IR spectroscopy to analyze biological materials. *Nat. Protoc.* 9, 1771-91 (2014).
21. Li, G. Removing background of Raman spectrum based on wavelet transform. 2009 *Int. Conf. Futur. Comput. Commun. FCC* 2009 198-200 (2009). doi:10.1109/FCC.2009.69
22. Clupek, M., Matejka, P. & Volka, K. Noise reduction in Raman spectra: Finite impulseresponse filtration versus Savitzky-Golay smoothing. *J. Raman Spectrosc.* 38, 1174-1179 (2007).
23. Keller, M. D., Kanter, E. M. & Mahadevan-jansen, A. Raman Spectroscopy for Cancer Diagnosis. *spectroscopy* 21, (2006).
24. Kanter, E. M. et al. Application of Raman spectroscopy for cervical dysplasia diagnosis. *J. Biophotonics* 2, 81-90 (2009).
25. Kanter, E. M. et al. Multiclass discrimination of cervical precancers using Raman spectroscopy. *J. Raman Spectrosc.* 40, 205-211 (2009).
26. Savitzky, A. & Golay, M. J. E. Smoothing and Differentiation of Data by Simplified Least Squares Procedures. *Anal. Chem.* 36, 1627-1639 (1964).
27. Knief, P. Interactions of Carbon Nanotubes With human lung epithelial cells in vitro, Assessed by Raman Spectroscopy Thesis submitted by. (2010).
28. Christensen, W. F. *Methods of Multivariate Analysis. Third Edition.* (2012).
29. Matthews, Q., Brolo, A., Lum, J., Duan, X. & Jirasek, A. Raman spectroscopy of single human tumour cells exposed to ionizing radiation in vitro. *Phys. Med. Biol.* 56, 19-38 (2011).
30. Katainen, E. et al. Quantification of the amphetamine content in seized street samples by Raman spectroscopy. *J. Forensic Sci.* 52, 88-92 (2007).
31. Ghomi, M. in *Applications of Raman Spectroscopy to Biology: From Basic Studies to Disease Diagnosis* (2012).
32. Villasana, L., Dayger, C. & Raber, J. Dose- and ApoE Isoform-Dependent Cognitive Injury after Cranial (56)Fe Irradiation in Female Mice. *Radiat. Res.* 179, 493-500 (2013).
33. Acevedo, S. E., McGinnis, G. & Raber, J. Effects of 137Cs gamma irradiation on cognitive performance and measures of anxiety in Apoe−/− and wild-type female mice. *Radiat. Res.* 170, 422-8 (2008).
34. Villasana, L., Acevedo, S., Poage, C. & Raber, J. Sex-and APOE isoform-dependent effects of radiation on cognitive function. *Radiat. Res.* 166, 883-891 (2006).
35. Rendleman, J. et al. Genetic variation in DNA repair pathways and risk of non-Hodgkin's lymphoma. *PLoS One* 9, e101685 (2014).
36. Justice, T., Martenson, J., Wiseman, G. & Witzig, T. Safety and efficacy of external beam radiation therapy for non-Hodgkin lymphoma in patients with prior 90Y-ibritumomab tiuxetan radioimmunotherapy. *Cancer* 107, 433-438 (2006).
37. Jaime Garcia, H. Chromosomal sensitivity to X-rays in lymphocytes from patients with Turner syndrome. *Mutat. Res.* 160, 33-38 (1986).
38. Saraswathy, R., Meena, J. & Marimuthu, K. THE IMPORTANCE OF THE STUDY OF RADIOSENSITIVITY IN HUMAN GENETIC DISORDERS. *Int. J Pharma Bio Sci.* 3, 689-697 (2012).

39. Stone, N., Kendal, I C., Smith, J., Crow, P. & Barr, H. Raman spectroscopy for identification of epithelial cancers. *Faraday Discuss.* 141-57 (2004).
40. Notingher, I. et al. Discrimination between ricin and sulphur mustard toxicity in vitro using Raman spectroscopy. *J. R. Soc. Interface* 1, 79-90 (2004).
41. Krafft, C., Neudert, L., Simat, T. & Salzer, R. Near infrared Raman spectra of human brain lipids. *Spectrochim. Acta. A. Mol. Biomol. Spectrosc.* 61, 1529-35 (2005).
42. Huang, Z. et al. Near-infrared Raman spectroscopy for optical diagnosis of lung cancer. *Int. J. Cancer* 107, 1047-52 (2003).
43. Cheng, W.-T., Liu, M.-T., Liu, H.-N. & Lin, S.-Y. Micro-Raman spectroscopy used to identify and grade human skin pilomatrixoma. *Microsc. Res. Tech.* 68, 75-9 (2005).
44. Ruiz-Chica, A. J., Medina, M. A., Sanchez-Jimenez, F. & Ramirez, F. J. Characterization by Raman spectroscopy of conformational changes on guanine-cytosine and adenine-thymine oligonucleotides induced by aminooxy analogues of spermidine. *J. Raman Spectrosc.* 35, 93-100 (2004).
45. Dukor, R. K. Vibrational spectroscopy in the detection of cancer. *Handb. Vib. Spectrosc.* 3335-3361 (2002). doi: 10.1002/0470027320.s8107
46. Dieter Naumann. Infrared and NIR Raman spectroscopy in medical microbiology. *Proc. SPIE* 3257, *Infrared Spectrosc. New Tool Med.* 3257, (1998).
47. Sigurdsson, S. et al. Detection of skin cancer by classification of Raman spectra. *IEEE Trans. Biomed. Eng.* 51, 1784-1793 (2004).
48. Chan, J. W. et al. Micro-Raman spectroscopy detects individual neoplastic and normal hematopoietic cells. *Biophys. J.* 90, 648-56 (2006).
49. O Faolain, E. et al. A study examining the effects of tissue processing on human tissue sections using vibrational spectroscopy. *Vib. Spectrosc.* 38, 121-127 (2005).
50. Gniadecka, M., Wulf, H. C., Mortensen, N. N., Nielsen, O. F. & Christensen, D. H. Diagnosis of basal cell carcinoma by Raman spectroscopy., 28: 125-129. *J. Raman Spectrosc.* 28, 125-129 (1997).
51. Frank, C. J., McCreery, R. L. & Redd, D. C. Raman spectroscopy of normal and diseased human breast tissues. *Anal. Chem.* 67, 777-83 (1995).
52. Jyothi Lakshmi, R. et al. Tissue Raman spectroscopy for the study of radiation damage: brain irradiation of mice. *Radiat Res* 157, 175-182 (2002).
53. Fung, M. F. K., Senterman, M. K., Mikhael, N. Z., Lacelle, S. & Wong, P. T. T. Pressure-tuning Fourier transform infrared spectroscopic study of carcinogenesis in human endometrium. *Biospectroscopy* 2, 155-165 (1996).

The invention claimed is:

1. A prognostic method of analyzing a biological biofluid sample from a cancer patient to predict the patient's response to a specified modality of cancer treatment, the prognostic method comprising:
   obtaining diagnosis of a cancer patient, wherein the cancer is selected from esophageal cancer, colorectal cancer, prostate cancer, and breast cancer;
   obtaining the biological biofluid sample from the cancer patient;
   performing spectroscopy on the biological sample to obtain a spectrum; and
   comparing the obtained spectrum with one or more spectra from a pre-classified library to calculate a probability of a response to the specified modality of cancer treatment by the cancer patient.

2. The method of claim 1, wherein the modality of cancer treatment is selected from a group consisting of radiotherapy, chemotherapy, hormonal therapy, and radiotherapy combined with either chemotherapy or hormonal therapy.

3. The method of claim 1, wherein the modality of cancer treatment comprises radiotherapy.

4. The method of claim 1, wherein the biological biofluid sample is unirradiated.

5. The method of claim 1, wherein the biological biofluid sample is a blood sample.

6. The method of claim 5, comprising irradiating the in-vitro blood sample.

7. The method of claim 5, wherein:
   the blood sample is used whole and analyzed; or
   plasma or lymphocytes are extracted from the blood sample and analyzed.

8. The method of claim 7, wherein plasma is extracted and analyzed and the steps for analyzing the plasma are as follows:
   extracting plasma from the blood sample;
   depositing the plasma on a substrate;
   acquiring Raman/FTIR spectra;
   analyzing the obtained spectra by a statistical learning algorithm which compares the obtained spectra to spectra from a pre-classified library; and
   predicting response to therapy based on the analysis of the immediately preceding step.

9. The method of claim 7, wherein lymphocytes are extracted and analyzed and the steps for analyzing the lymphocytes are as follows:
   extracting lymphocytes from the blood sample;
   fixing the lymphocytes;
   depositing the fixed lymphocytes on a substrate;
   acquiring Raman/FTIR spectra;
   analyzing the obtained spectra by a statistical learning algorithm which compares the obtained spectra to spectra from a pre-classified library; and
   predicting response to therapy based on the analysis of the immediately preceding step.

10. The method of claim 1, wherein the biological biofluid sample is a blood lymphocyte sample.

11. The method of claim 10, comprising culturing blood lymphocyte cells as whole blood in-vitro.

12. The method of claim 1, wherein the spectroscopy is vibrational spectroscopy.

13. The method of claim 12, wherein the vibrational spectroscopy is performed using Raman spectroscopy or using FTIR spectroscopy.

14. The method of claim 1, wherein the response to cancer treatment comprises tumor regression.

15. The method of claim 1, wherein the response to cancer treatment comprises radiotherapeutic treatment toxicity or chemotherapeutic treatment toxicity.

16. The method of claim 1, wherein the comparing comprises the use of spectral decomposition followed by analysis by a classifier.

17. The method of claim 16, wherein the spectral decomposition comprises using principal component analysis (PCA) spectral decomposition.

18. The method according to claim 1, wherein the cancer is prostate cancer.

19. The method according to claim 1, wherein the method comprises monitoring the progress of treatment within the course of therapy using vibrational spectra of peripheral blood extracted from the patient.

20. A prognostic method of analyzing a biological sample from a cancer patient to predict the patient's response to a specified modality of cancer treatment, wherein the cancer comprises a solid tumor and a biopsy of the tumor has been taken, the prognostic method comprising:
- obtaining a diagnosis of a cancer patient;
- obtaining a sample from the tumor biopsy;
- subjecting the sample to fixation and paraffin embedding;
- performing microtoming on the sample;
- performing spectroscopy on the sample to acquire FTIR/Raman spectra;
- analyzing obtained images by a statistical learning algorithm which compares obtained spectra to spectra from a pre-classified library to calculate a probability of a response to the specified modality of cancer treatment by the cancer patient; and
- predicting response to therapy based on the analysis of the immediately preceding step.

* * * * *